(12) United States Patent
Willard

(10) Patent No.: US 11,969,185 B2
(45) Date of Patent: Apr. 30, 2024

(54) SOFT TISSUE CUTTING INSTRUMENT WITH SELF LOCKING, MULTI-POSITION, AND SLIDE BUTTON LINEARLY ACTUATED RETRACTABLE BLADE OR HOOK

(71) Applicant: Conmed Corporation, Utica, NY (US)

(72) Inventor: Benjamin Willard, Clearwater, FL (US)

(73) Assignee: Conmed Corporation, Utica, NY (US)

( * ) Notice: Subject to any disclaimer, the term of this patent is extended or adjusted under 35 U.S.C. 154(b) by 335 days.

(21) Appl. No.: 17/282,204

(22) PCT Filed: Oct. 2, 2019

(86) PCT No.: PCT/US2019/054273
§ 371 (c)(1),
(2) Date: Apr. 1, 2021

(87) PCT Pub. No.: WO2020/072628
PCT Pub. Date: Apr. 9, 2020

(65) Prior Publication Data
US 2021/0338264 A1  Nov. 4, 2021

Related U.S. Application Data

(60) Provisional application No. 62/740,500, filed on Oct. 3, 2018.

(51) Int. Cl.
*A61B 17/3211* (2006.01)
*A61B 17/00* (2006.01)

(52) U.S. Cl.
CPC . *A61B 17/3211* (2013.01); *A61B 2017/00367* (2013.01); *A61B 2017/32113* (2013.01)

(58) Field of Classification Search
CPC ........ A61B 17/320016; A61B 17/3209; A61B 17/3211; A61B 17/32; A61B 17/00;
(Continued)

(56) References Cited

U.S. PATENT DOCUMENTS 3,841,361 A * 10/1974 Kieronski ................. B21F 1/06
                                                              72/384
5,207,696 A    5/1993 Matwijcow
(Continued)

FOREIGN PATENT DOCUMENTS

JP   2003504109 A    2/2003
JP   2006524113     10/2006
(Continued)

OTHER PUBLICATIONS

EP Communication 161(1) and 162 EPC, App. No. 19791397.3, pp. 1-2, dated May 14, 2021.
(Continued)

*Primary Examiner* — Jocelin C Tanner
(74) *Attorney, Agent, or Firm* — Bond, Schoeneck & King, PLLC; Frederick J. M. Price

(57) ABSTRACT

A system and method for cutting soft tissue with a retractable surgical cutting device. The device includes a handle, an actuator positioned thereon, and a sheath attached thereto, where the sheath surrounds a shaft with a blade attached to the distal end thereof. The device also includes a drive and locking mechanism connected to the actuator and to the shaft within the internal space of the handle, wherein the drive and locking mechanism is configured to move the shaft in the first direction and lock the shaft in the shaft first position in response to movement of the actuator in one of the first direction or the second direction, and wherein the drive mechanism is configured to move the shaft in the second direction and lock the shaft in the shaft second position in response to movement of the actuator in the other one of the first direction or the second direction.

12 Claims, 24 Drawing Sheets

(58) Field of Classification Search
CPC .............. A61B 90/08; A61B 90/00; A61B 2017/00367; A61B 2017/00407; A61B 2017/32113; A61B 2090/08021; H01H 3/44; F16H 29/00
See application file for complete search history.

(56) References Cited

U.S. PATENT DOCUMENTS

| | | | |
|---|---|---|---|
| 5,403,337 A | 4/1995 | Platts | |
| 5,475,925 A | 12/1995 | Newman et al. | |
| 5,481,804 A | 1/1996 | Platts | |
| 5,571,127 A | 11/1996 | Decampli | |
| 5,599,351 A | 2/1997 | Haber et al. | |
| 5,904,699 A | 5/1999 | Schwemberger et al. | |
| 5,908,432 A | 6/1999 | Pan | |
| 6,510,754 B2 | 1/2003 | Yan et al. | |
| 6,623,499 B1 | 9/2003 | Andreini et al. | |
| 7,101,382 B2 | 9/2006 | George et al. | |
| 7,159,713 B1 | 1/2007 | Austria | |
| 7,387,637 B2 | 6/2008 | Morawski et al. | |
| 7,445,622 B2 | 11/2008 | Ortiz et al. | |
| 7,465,288 B2 | 12/2008 | Dudney et al. | |
| 8,080,004 B2 | 12/2011 | Downey et al. | |
| 8,490,713 B2 | 7/2013 | Furnish et al. | |
| 8,500,789 B2 | 8/2013 | Wuebbeling et al. | |
| 8,567,070 B2 | 10/2013 | Rowlay et al. | |
| 8,769,826 B2 | 7/2014 | Wu | |
| 8,776,380 B1 | 7/2014 | Quimby et al. | |
| 8,777,929 B2 | 7/2014 | Schneider et al. | |
| 8,887,717 B2 | 11/2014 | Levitan | |
| 9,050,067 B2 | 6/2015 | Duncan et al. | |
| 9,113,967 B2 | 8/2015 | Soubeiran | |
| 9,421,115 B2 | 8/2016 | Wübbeling et al. | |
| 9,451,951 B2 | 9/2016 | Sullivan et al. | |
| 9,526,498 B2 | 12/2016 | Reed | |
| 9,615,824 B2 | 4/2017 | Furnish et al. | |
| 9,668,732 B2 | 6/2017 | Patel et al. | |
| 9,694,159 B2 | 7/2017 | Schneider et al. | |
| 9,918,801 B2 | 3/2018 | Takei | |
| 10,022,110 B2 | 7/2018 | Stand, III et al. | |
| 10,123,815 B2 | 11/2018 | Huffenus et al. | |
| 10,123,834 B2 | 11/2018 | Schiele et al. | |
| 10,342,520 B2 | 7/2019 | Hess et al. | |
| 10,588,627 B2 | 3/2020 | Sniffin et al. | |
| 10,595,866 B2 | 3/2020 | Patel et al. | |
| 10,737,062 B2 | 8/2020 | Schneider et al. | |
| 2005/0033336 A1 | 2/2005 | Yang | |
| 2006/0235431 A1 | 10/2006 | Goode et al. | |
| 2006/0241664 A1 | 10/2006 | Lam | |
| 2007/0027468 A1 | 2/2007 | Wales et al. | |
| 2009/0187168 A1* | 7/2009 | Maeda | A61M 25/0113 606/1 |
| 2009/0192538 A1 | 7/2009 | Sandel et al. | |
| 2014/0128889 A1* | 5/2014 | Sullivan | A61B 17/0483 606/144 |
| 2015/0080911 A1* | 3/2015 | Reed | A61B 17/068 606/139 |
| 2015/0216585 A1 | 8/2015 | Kirstgen et al. | |
| 2016/0166240 A1 | 6/2016 | Vetter et al. | |
| 2016/0235430 A1* | 8/2016 | Huffenus | A61B 17/3211 |
| 2016/0287248 A1 | 10/2016 | Levin et al. | |

FOREIGN PATENT DOCUMENTS

| | | |
|---|---|---|
| JP | H10508510 A | 1/2008 |
| JP | 2015147044 | 8/2016 |
| KR | 10-2018-0037415 | 4/2015 |
| WO | WO1993021837 A1 | 11/1993 |
| WO | 1993/25152 | 12/1993 |
| WO | 2001/054588 | 8/2001 |
| WO | WO 01/54588 | 8/2001 |
| WO | 2005/0033336 | 4/2005 |
| WO | 2013/134489 | 9/2013 |
| WO | WO 2013/134489 | 9/2013 |
| WO | 2016/160581 | 10/2016 |
| WO | WO 2016/160581 | 10/2016 |

OTHER PUBLICATIONS

EU Communication 94(3), App. No. 19791397.3, dated May 19, 2022, pp. 1-6.
International Search Report Form PCT/ISA/220, International Application No. PCT/US2019/054273, pp. 1-18, dated Nov. 27, 2019.
International Search Report Form PCT/ISA/220, International Application No. PCT/US2018/036414, pp. 1-13, dated Aug. 14, 2018.
JP Office Action, App. No. 2021-518163, pp. 1-12, dated Mar. 29, 2022.
EP Communication 94(3), App No. 18735055.8, dated Oct. 6, 2022, pp. 1-7.
JP Office Action, App. No. 2019-568244, pp. 1-6, dated May 11, 2021.
CA Office Action, App. No. 3066370, dated Aug. 29, 2022, pp. 1-4.
KR Preliminary Rejection and translation, App. No. 10-2021-7011539, pp. 1-16, dated May 4, 2023.
"Translated KR Notice of Preliminary Rejection, Application No. 10-2021-7011539, pp. 3-10, dated Oct. 25, 2023", Translated KR Notice of Preliminary Rejection, Application No. 10-2021-7011539, pp. 3-10, dated Oct. 25, 2023.

* cited by examiner

SOFT TISSUE CUTTING INSTRUMENT WITH SELF LOCKING, MULTI-POSITION, AND SLIDE BUTTON LINEARLY ACTUATED RETRACTABLE BLADE OR HOOK

CROSS-REFERENCES TO RELATED APPLICATIONS

This application is a national stage application under 35 U.S.C. 371 based on international patent application PCT/US19/54273 filed on Oct. 2, 2019, which relates and claims priority to U.S. Provisional Patent Application Ser. No. 62/740,500 filed on Oct. 3, 2018. The present application also relates to PCT/US18/36414, which claims priority to U.S. Provisional Patent Application Ser. No. 62/518,803 filed Jun. 13, 2017, 62/524,769 filed Jun. 26, 2017, 62/597,612 filed Dec. 12, 2017 and 62/652,365 filed Apr. 4, 2018, the entireties of which are incorporated herein by reference.

BACKGROUND OF THE INVENTION

1. Field of the Invention

The invention relates generally to surgical device for cutting soft tissue and more particularly, a soft tissue cutting instrument with a retractable blade or hook

2. Description of Related Art

During surgery, soft tissue is incised by inserting a cutting device with a surgical blade or hook blade into a surgical site within the body. Some current cutting devices have an exposed surgical blade or hook blade. If the blade on the cutting device is exposed, there is a potential of injury to both the user and the patient. In one example, the user is at risk of injury from the exposed blade while handling the cutting device. In another example, the patient is at risk of injury when the exposed blade enters or exits the body. When an exposed blade enters or exits the body, it may inadvertently cut soft tissue.

In addition, current cutting devices are not ergonomically designed for the user, which may also contribute to mishandling and risk injury of the user and the patient.

Therefore, there is a need for an easy-to-use surgical instrument for cutting soft tissue that has a protectable blade or hook blade.

In addition, in the field of handheld manually actuated medical instruments, it is often desired to have the device actuated by the thumb/finger(s) of the user resulting in two or more discrete positions of one or more components relative to each other. Furthermore, it is often desired to have these positions maintained even after the finger/thumb of the user is removed from the button/switch/lever/slide/etc. of the instrument. Additionally, it is often desired to have the instrument maintain these positions of components even if the instrument is acted upon by outside forces other than those applied by the user of the instrument for the purposes of actuating or de-actuating the instrument, such as the reaction forces the instrument may encounter when performing work on the subject (the patient, another medical device, etc.). The inventors of the current disclosure have recognized that without a locking mechanism, such forces could potentially "back drive" the instrument into an undesired condition of actuation/de-actuation.

While a number of mechanisms exist to "lock" the user-instrument interface to prevent back-driving of a mechanism within such an instrument, all have drawbacks. For example, A friction "detent" is a common means to "lock" a mechanism into a particular location/configuration. However, since friction performs the holding of the element (s) of the mechanism in place, this holding ability can be overpowered by outside forces greater in magnitude than the friction forces in the detent mechanism. A "lock button" that holds, locks, or otherwise "pins into place" a user interface actuator such as a slide, a trigger, or a lever provides a positive locking of the interface that is resistant to back-driving when outside forces are applied. However, actuating the "lock button" itself requires the user to perform a second action in addition to the main action of using the interface itself. Additionally, the user must be mindful to remember to de-actuate the "lock button" before attempting to de-actuate the instrument or else de-actuation could be impossible (at least without breaking or deforming the mechanism). A "gated shifter" type of actuator, where during the course of actuation, there are one or more laterally offset "parking locations" into which the actuator engages, preventing the actuator from being actuated any further and preventing the mechanism(s) from being back-driven by outside forces, can be used. However, the lateral motion needed to place the actuator into one of the "parking locations" isn't left-right handed universal. While a right-handed user may be able to quickly flick an actuator one direction laterally, a left-handed user may find it more difficult to perform the same actuation in the same direction (same direction with respect to the instrument). Further, motions along multiple separate axes (e.g., longitudinal and lateral) may prove to be difficult and/or cause issues during a medical procedure, where movement along a single axis (linear movement) would be easier for a user.

Therefore, there is a need for a mechanism that allows for actuation of a medical device and locking of the same per movement of an actuator along a single axis (linear movement).

Description of the Related Art Section Disclaimer: To the extent that specific patents/publications/products are discussed above in this Description of the Related Art Section or elsewhere in this disclosure, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

The present invention is directed to, inter alia, a system and method for cutting tissue with a retractable surgical cutting device. In one embodiment, the present invention is a retractable surgical cutting device. The device includes a handle having a first channel extending therethrough. A switch located on the handle, the switch being movable between a retracted position and an extended position. An actuator extends through the first channel and connects to the switch within the handle. The actuator also comprises a blade at its distal end. The blade can include, but is not limited to, any shaped blade including a straight blade, angled blade (angled from itself and/or the shaft), curved blade (curved from itself and/or the shaft) or a hook blade etc. An outer sheath is connected to the handle and surrounds the actuator and at least a portion of the blade. A drive mechanism is connected to the switch within the handle such that when the switch moves from the retracted position to the extended position, the actuator moves from a retracted position to an extended position. When the actuator is in the retracted position, the blade can be (although does not have to be) entirely within the outer sheath (as in a preferred embodiment), and when the actuator is in the extended position, at least a portion of the blade is out of the outer sheath.

In another embodiment of the device, the device includes a handle having a first channel extending therethrough and a switch located thereon. The switch is movable between a retracted position and an extended position. An actuator extends through the first channel and connects to a proximal end of the first channel within the handle. The actuator has a blade at its distal end. An outer sheath surrounds the actuator and at least a portion of the blade. The outer sheath interfaces with the switch. A drive mechanism is connected to the switch within the handle such that when the switch moves from the retracted position to the extended position, the outer sheath moves from a retracted position to an extended position. When the outer sheath is in the retracted position, the blade is fully positioned within (although does not have to be) the outer sheath (as in a preferred embodiment) and when the outer sheath is in the extended position, at least a portion of the blade is positioned outside of the outer sheath.

In one embodiment, the present invention provides a method for cutting tissue. The method comprises the steps of: (i) providing a retractable surgical cutting device having a handle with a first channel extending therethrough, a switch located on the handle which is movable between a retracted position and an extended position, an actuator which extends to a proximal end of the first channel, a blade at a distal end of the actuator, an outer sheath interfacing the switch, the outer sheath surrounding the actuator and at least a portion of the blade; and a drive mechanism connected to the switch within the handle; (ii) moving the switch in a first direction along a longitudinal x-axis extending through the device; (iii) moving the outer sheath, via the drive mechanism, relative to the actuator; and (iv) exposing at least a portion of the blade. The method can further include the steps of advancing the outer sheath into a surgical site, and cutting tissue at a surgical site with the blade.

In a further embodiment of the device, the device includes a handle including a handle proximal end, a handle distal end, an outer surface, and an internal space, the handle extending along a central longitudinal axis; an actuator located and movable in a first direction to a first actuator position and in a second direction to a second actuator position on the outer surface of the handle; a sheath extending along the central longitudinal axis and including a sheath proximal end and a sheath distal end, wherein the sheath proximal end is positioned within the internal space of the handle, and wherein the sheath is configured to move in the first direction to a sheath first position, and is configured to move in a second direction to a sheath second position; a shaft at least partially positioned within the sheath and extending along the central longitudinal axis and including a shaft proximal end and a shaft distal end, wherein the shaft proximal end is connected to the interior surface of the handle and the shaft distal end includes a blade; and a drive and locking mechanism connected to the actuator and to the sheath within the internal space of the handle, wherein the drive and locking mechanism is configured to move the sheath in the first direction and lock the sheath in the sheath first position in response to movement of the actuator in one of the first direction or the second direction, and wherein the drive mechanism is configured to move the sheath in the second direction and lock the sheath in the sheath second position in response to movement of the actuator in the other one of the first direction or the second direction.

In an additional embodiment of the device, the device includes a handle including a handle proximal end, a handle distal end, an outer surface, and an internal space, the handle extending along a central longitudinal axis; an actuator located and movable in a first direction to a first actuator position and in a second direction to a second actuator position on the outer surface of the handle; a sheath extending along the central longitudinal axis and including a sheath proximal end and a sheath distal end, wherein the sheath proximal end is positioned within the internal space of the handle, and wherein the proximal end of the sheath is connected to the interior surface of the handle; a shaft at least partially positioned within the sheath and extending along the central longitudinal axis and including a shaft proximal end and a shaft distal end, wherein the shaft is configured to move in the first direction to a shaft first position, and is configured to move in a second direction to a shaft second position; and a drive and locking mechanism connected to the actuator and to the shaft within the internal space of the handle, wherein the drive and locking mechanism is configured to move the shaft in the first direction and lock the shaft in the shaft first position in response to movement of the actuator in one of the first direction or the second direction, and wherein the drive mechanism is configured to move the shaft in the second direction and lock the shaft in the shaft second position in response to movement of the actuator in the other one of the first direction or the second direction.

In accordance with an embodiment, the actuation and locking mechanism achieves a primary technical outcome of allowing the user to lock an actuated component of a handheld, manually-actuated surgical instrument at either end of a range of travel, to prevent "back-driving" of any components, locking them in place without need to perform any other additional actions or motions, or to interface with any other switches or buttons to "lock" the actuation into place. In one embodiment, the locking is not performed by friction, resulting in a resistance to back-driving any components of the device by overpowering any friction that may be used to temporarily hold the device in a particular state of actuation/de-actuation. This positive, mechanical, locking function is entirely integral to the exact same motion that is used to bring about the actuation/de-actuation of the instrument.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following description taken in conjunction with the accompanying drawings in which:

DETAILED DESCRIPTION OF THE INVENTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Figure 1:
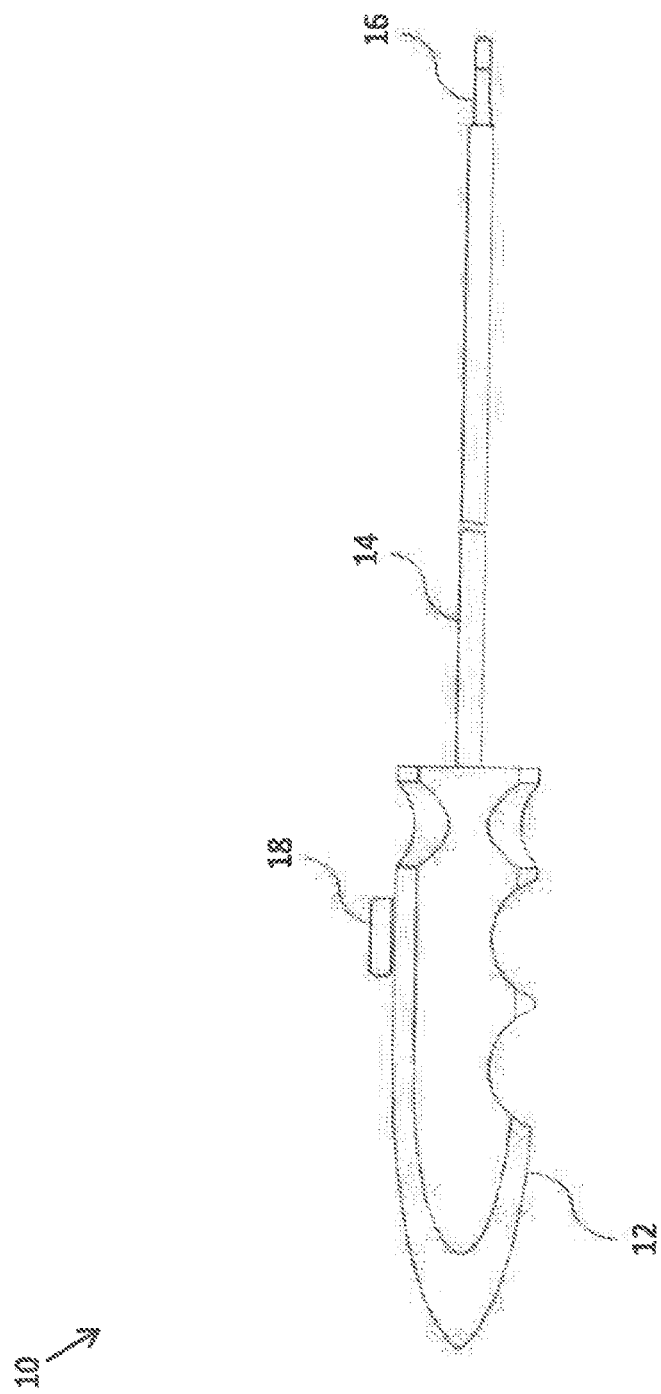
FIG. 1 is a side view schematic representation of an illustrative embodiment of a retractable surgical cutting device.

Referring now to FIG. 1, there is shown a side view schematic representation of an illustrative embodiment of a retractable surgical cutting device 10. The device 10 comprises a handle 12 connected to an outer sheath 14, which extends to a distal blade 16. The blade 16 is selectively extended and retracted upon actuation of an actuator (e.g., button, switch, lever, or knob) 18 on the handle 12, as will be explained in detail later. As shown in FIG. 1, the handle 12 can include thumb and finger grooves such that the shape of the handle 12 is ergonomic. The ergonomic design of the handle 12 provides increased control of the device 10 for its intended use. In other embodiments, the handle 12 may have fewer grooves or no grooves entirely. In some embodiments, the handle 12 is composed of plastic; however, the handle 12 may be composed of stainless steel or other traditional materials suitable for surgical devices.

Figure 2:
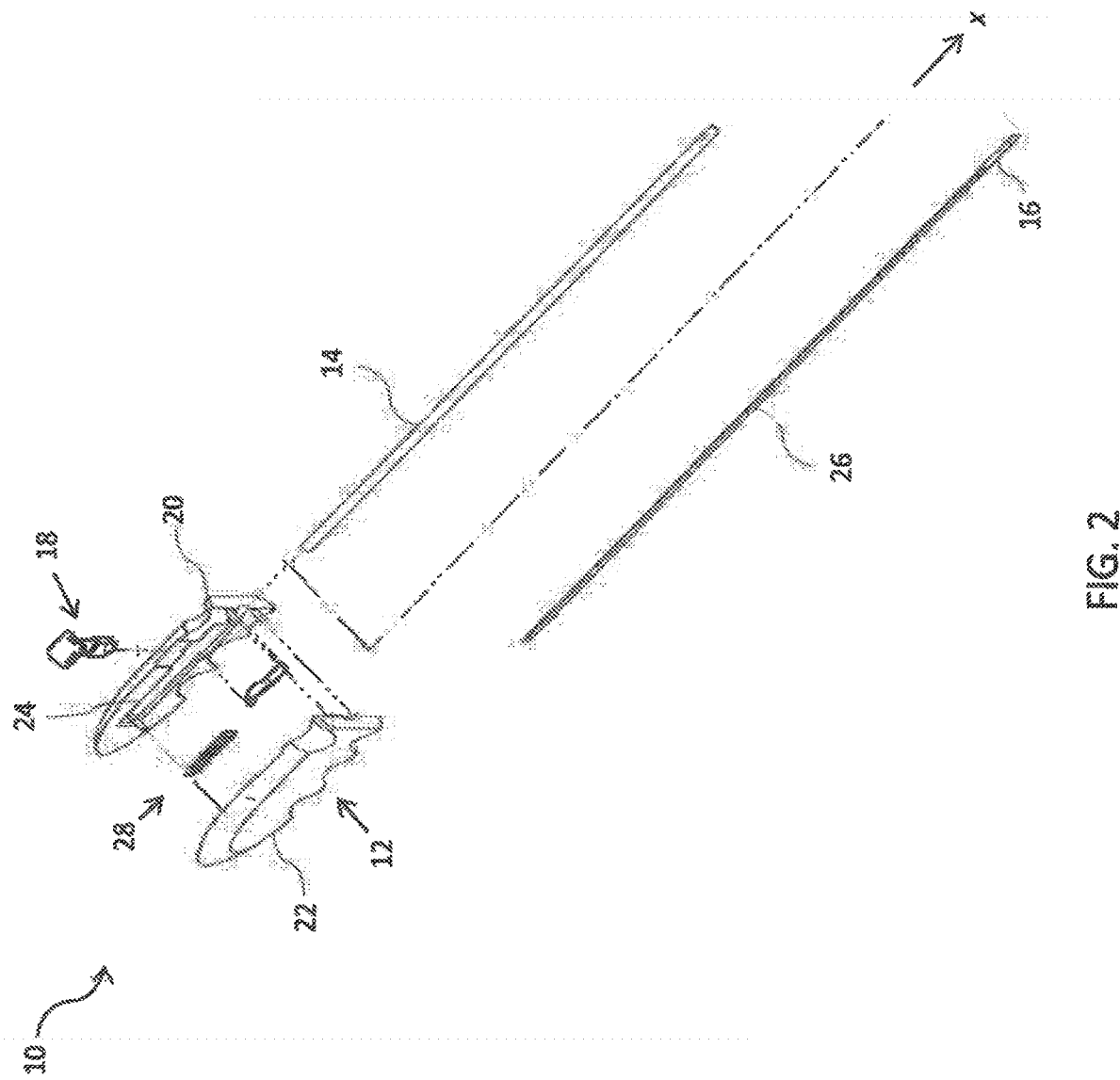
FIG. 2 is an exploded perspective view schematic representation of an illustrative embodiment of the retractable surgical cutting device of FIG. 1.

Turning now to FIG. 2, there is shown an exploded view schematic representation of the illustrative embodiment the retractable surgical cutting device 10 of FIG. 1. In the depicted embodiment, the handle 12 of the device 10 is comprised of two pieces, a first piece 20 and a second piece 22, having one or more channels therethrough. It is contemplated that in an alternative embodiment, the handle 12 may be composed of a single piece molded or otherwise formed around the inner components of the handle 12. Continuing with FIG. 2, the handle 12 comprises a first channel 24, which is sized, dimensioned, and otherwise configured for an actuator 26, which is connected to the blade 16. The actuator 26 moves longitudinally within the outer sheath 14 in both directions along an x-axis, which extends approximately through the center of the handle 12. The longitudinal movement of the actuator 26 is caused by a drive mechanism 28 within the handle 12, as will be described in detail later. In other embodiments, the actuator 26 remains stationary while the drive mechanism 28 moves the outer shaft 14 relative to the actuator 26 and the blade 16. In the one embodiment, the actuator 26 comprises the blade 16 machined on its distal end 30. Thus, the embodiment of the actuator 26 and blade 16 can be a single-piece embodiment.

Figure 3B:
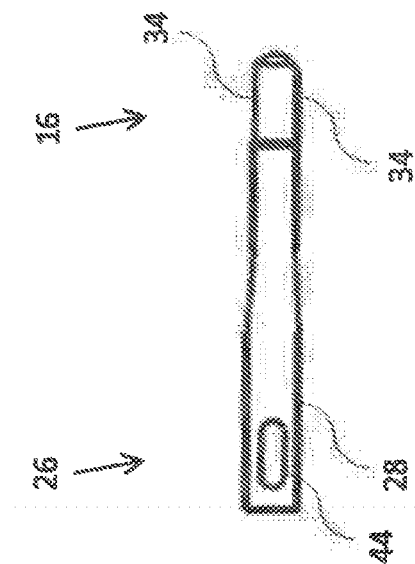
FIG. 3B is a top view schematic representation of an illustrative embodiment of a blade.
Figure 3A:
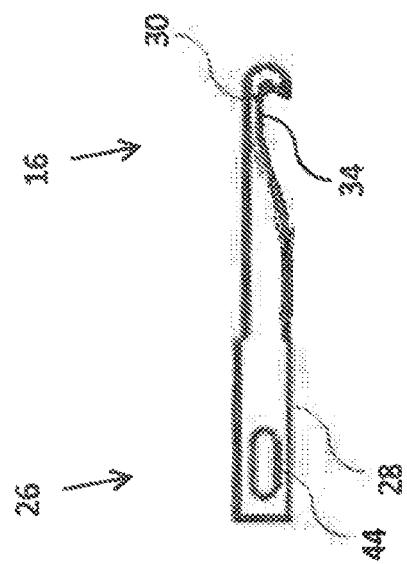
FIG. 3A is a top view schematic representation of an illustrative embodiment of a hook blade.

Referring now to FIGS. 3A-3B, there are shown top view schematic representations of illustrative embodiments of a blade. The blade 16 in FIGS. 3A-3B comprises an aperture 44 for connecting to the actuator 26 in a two-piece embodiment of the actuator 26 and blade 16. FIG. 3A shows an embodiment wherein the blade 16 is a hook blade having at least one sharp edge 34 and one non-sharp edge 30. FIG. 3B shows an embodiment wherein the blade 16 is a surgical blade with two sharp edges 34 (e.g., top and bottom). Any combination and number of sharp edges 34 and/or non-sharp edges 30 is contemplated for the blade 16.

Figure 4:
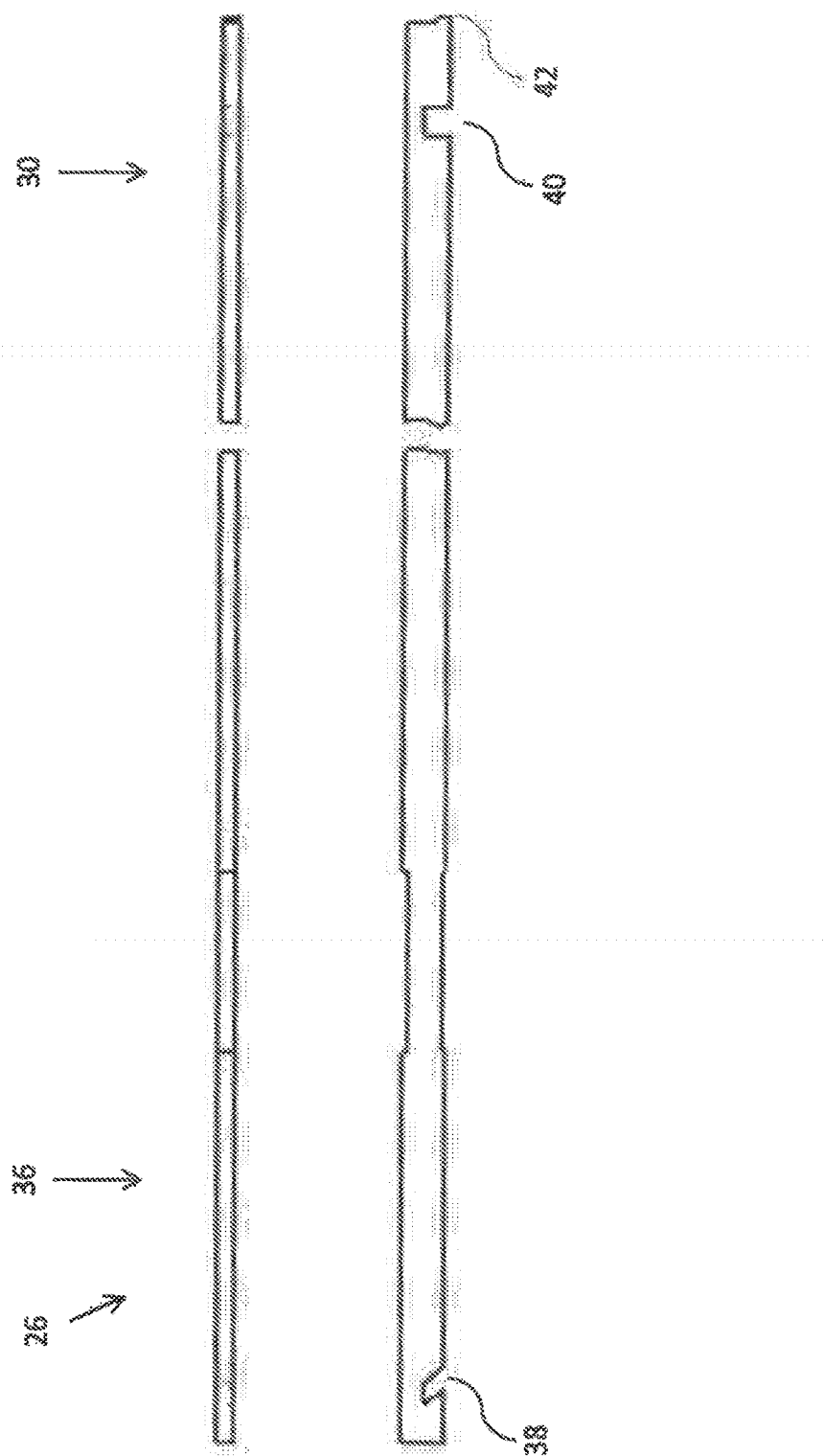
FIG. 4 is a top view and side view schematic representation of an illustrative embodiment of a two-piece actuator.

Referring now to FIG. 4, there is shown a top and side view schematic representation of an illustrative embodiment of the actuator 26 of a two-piece actuator 26 and blade 16. In comparison to a one-piece actuator 26 including the blade 16, the actuator 26 of FIG. 4 is separate from and not otherwise machined onto the blade 16. The actuator 26 in FIG. 4 comprises one or more notches for connecting to the blade 16 and the drive mechanism 28. At the proximal end 36 of the actuator 26 there is a notch 38 for connecting the actuator 26 to the drive mechanism 28. In another embodiment, the notch 38 at the proximal end 36 may be an aperture or other means for attaching the drive mechanism 28 to the actuator 26. The actuator 26 can also comprise one or more notches 40, 42 at its distal end 30. The notches 40, 42 at the distal end 30 of the actuator 26 are configured for attachment to the blade 16.

Figure 5B:
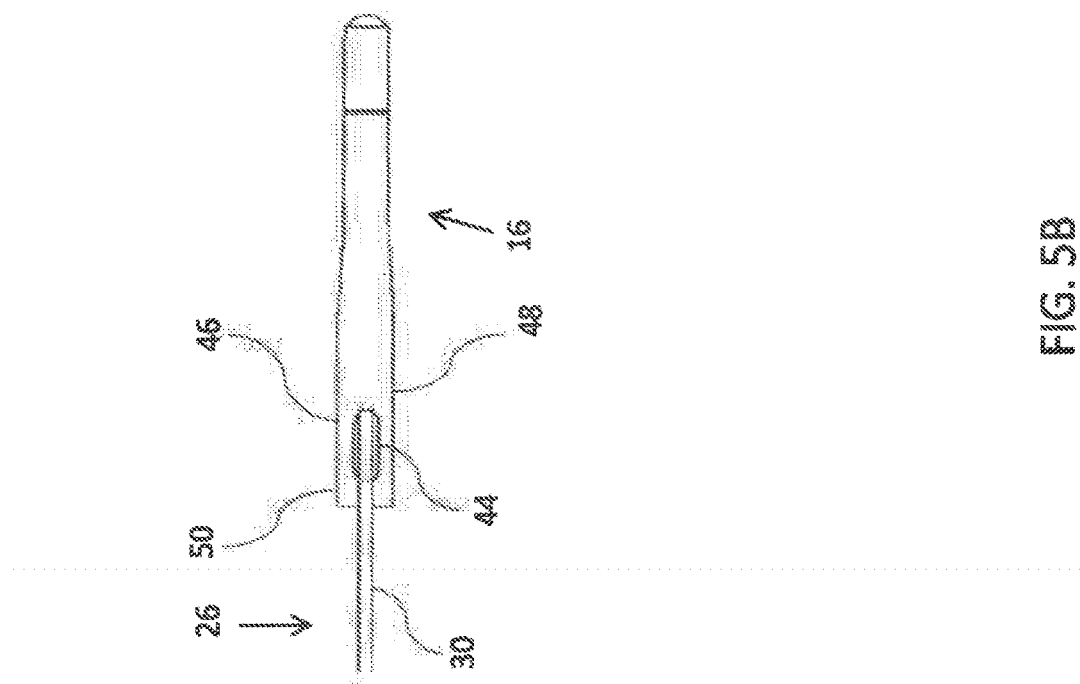
FIG. 5B is a top view schematic representation of an illustrative embodiment of the two-piece actuator of FIG. 4 connected to a blade.
Figure 5A:
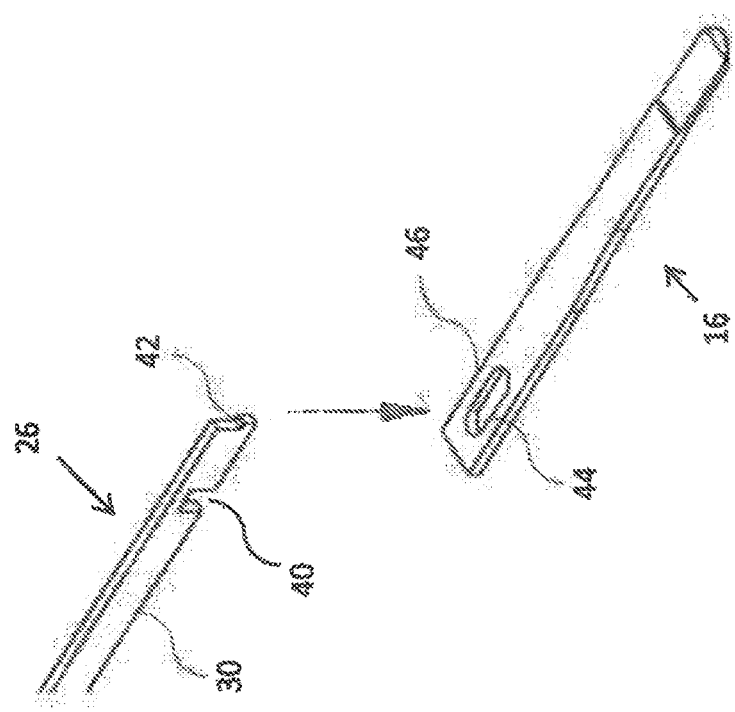
FIG. 5A is a perspective view schematic representation of an illustrative embodiment of the two-piece actuator of FIG. 4 and a blade.
Figure 5D:
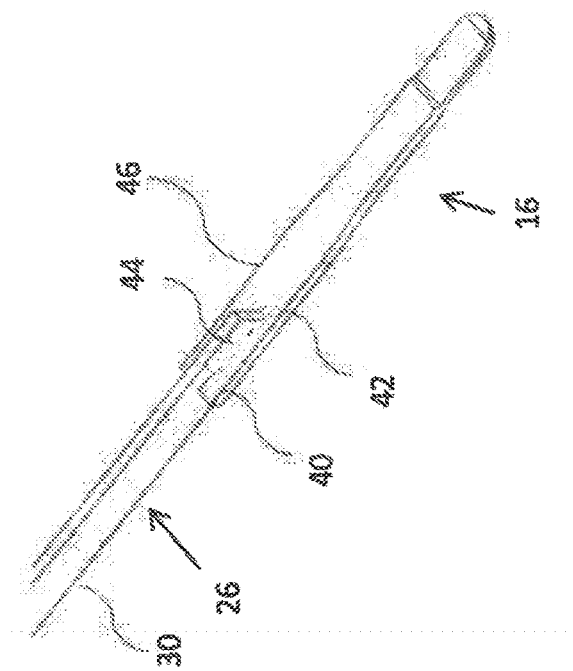
FIG. 5D is a perspective view schematic representation of an illustrative embodiment of the two-piece actuator of FIG. 4 connected to a blade.
Figure 5C:
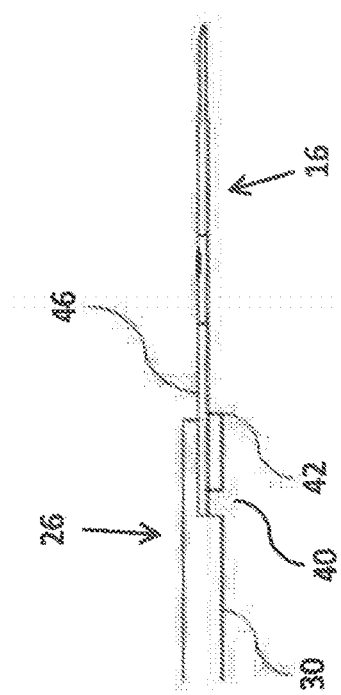
FIG. 5C is a side view schematic representation of an illustrative embodiment of the two-piece actuator of FIG. 4 connected to a blade.

Turning now to FIGS. 5A-5D, there are shown various views of schematic representations of an illustrative embodiment of the distal end 30 of the two-piece actuator 26 and blade 16. As shown in FIG. 5A, the distal end 30 of the actuator 26 has a first notch 40 and a second notch 42, while the blade 16 has an aperture 44 at its proximal end 46. In the depicted embodiment, the first notch 40 and the second notch 42 have recesses which extend in directions opposing each other. To assemble the two-piece actuator 26 and blade 16, the distal end 30 of the actuator 26 is inserted at an angle into the aperture 44 at the proximal end 46 of the blade 16. The distal end 30 of the actuator 26 is so inserted until the second notch 42 is through the aperture 44. Thereafter, the proximal end 36 of the actuator 26 (shown in FIG. 4) is rotated away from the blade 16 and into the same plane as the blade 16, locking the blade 16 into place, as shown in FIGS. 5C-5D. The second notch 42 on the distal end 30 of the actuator 26 engages the blade 16 on a distal side 48 of the aperture 44, while the first notch 40 engages the blade 16 on a proximal side 50 of the aperture 44, as shown in FIG. 5B.

Figure 6:
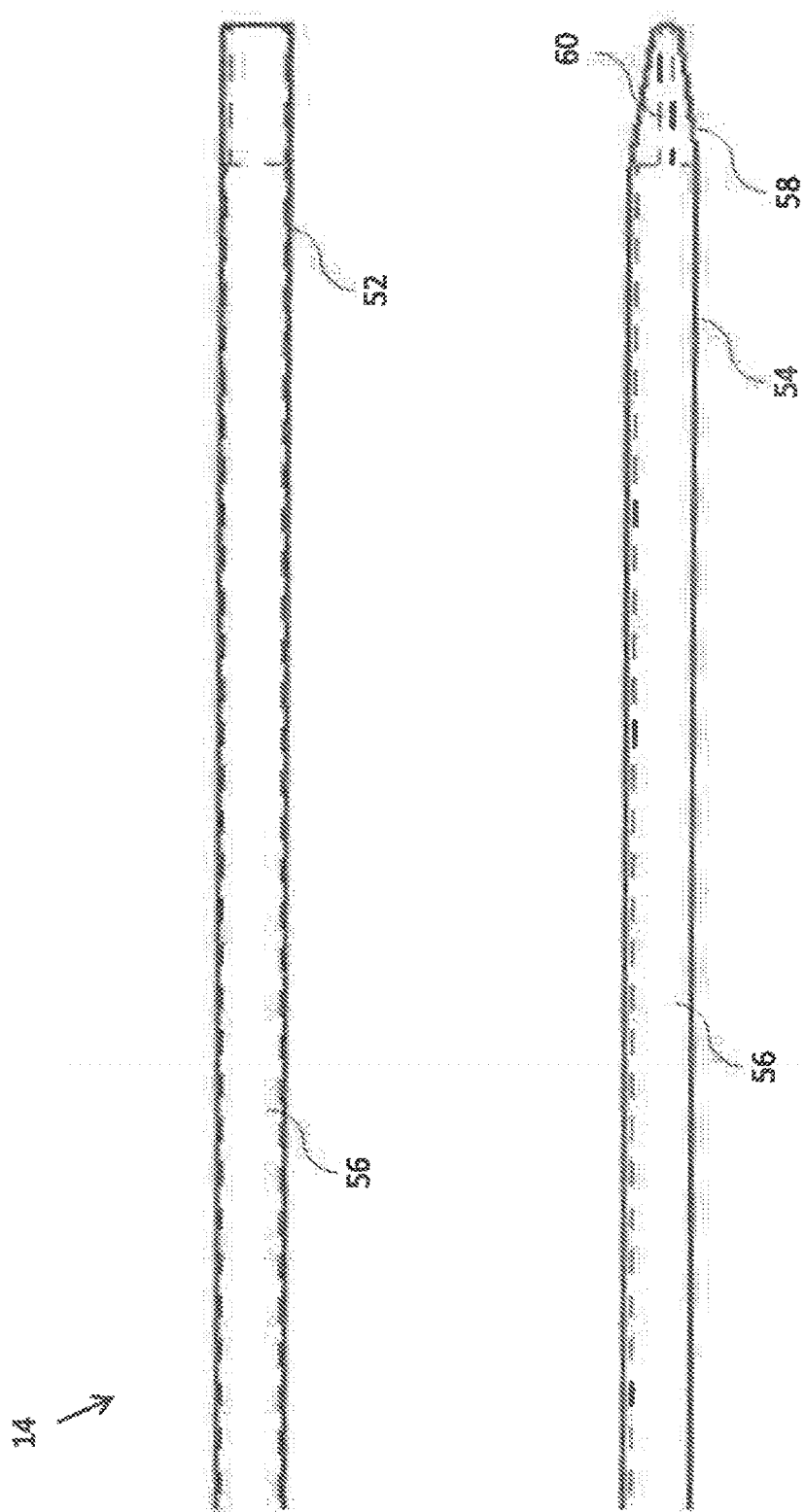
FIG. 6 is a side view schematic representation of an illustrative embodiment of the outer sheath.

Referring now to FIG. 6, there is shown a top view schematic representation of an illustrative embodiment of a proximal end 52 and a distal end 54 of an outer sheath 14. In the depicted embodiment, the outer sheath 14 is cannulated such that the outer sheath 14 has a first inner volume 56. The outer sheath 14 is sized and dimensioned to fit around the actuator 26 and at a least a portion of the blade 16. In other words, the actuator 26 and the blade 16 are inserted into the first inner volume 56 of the outer sheath 14 such that the outer sheath 14 surrounds the actuator 26 and at least a portion of the blade 16 (as shown in FIG. 1). The outer sheath 14 is fixed to the handle 12 of the device 10 such that the longitudinal movement of the actuator 26 (via the drive mechanism 28) extends and retracts the blade 16 from the outer sheath 14. In alternative embodiments, the outer sheath 14 is fixed to the switch 18 and longitudinal movement of the switch along the x-axis moves the outer sheath 14 relative to a stationary actuator 26 and blade 16.

FIG. 6 also shows an embodiment wherein the outer sheath 14 has a narrow portion 58. The narrow portion 58 of the outer sheath 14 has a second inner volume 60 with a diameter smaller than the diameter of the first inner volume 56 of the outer sheath 14. In one embodiment, the narrow portion 58 is tapered in a direction toward the distal end 30 of the actuator 26 and blade 16, as shown in FIG. 6. However, the narrow portion 58 does not need to be tapered in order to have a second inner volume 60 with a diameter smaller than the diameter of the first inner volume 56. The narrow portion 58 having a second inner volume 60 with a smaller diameter aids in preventing the potential of the blade 16 from inadvertently becoming disconnected from the actuator 26 (in the two-piece embodiment). The narrow portion 58 can also provide an a-traumatic tip to prevent damage at or near the surgical site based on its shape and/or being composed of non-metal material, such as PEEK. In the event of a failure of the notches 40, 42 securing the blade 16 to the actuator 26, the narrow portion 58 and the second inner volume 60 maintain the blade 16 within the outer sheath 14 as opposed to falling from the device 10.

Figure 7:
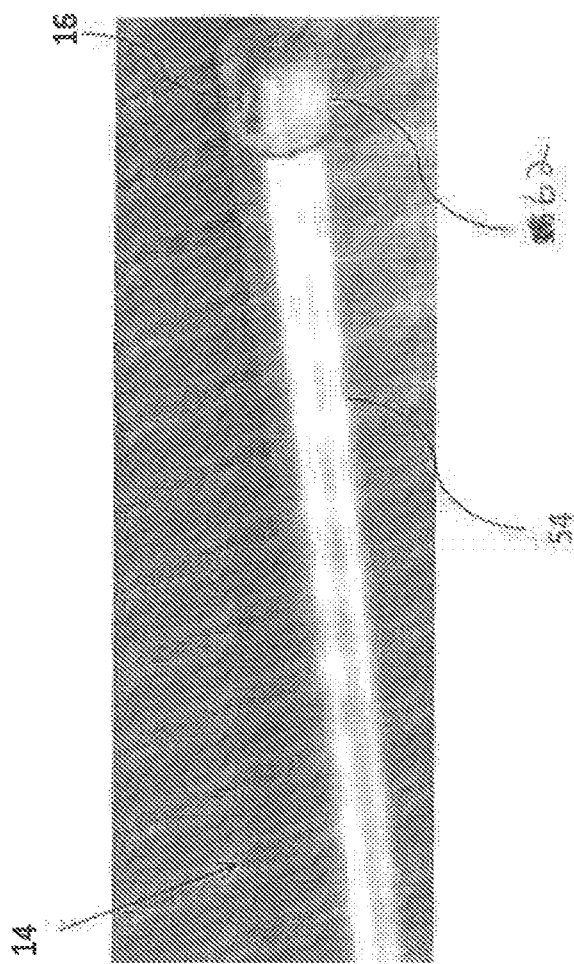
FIG. 7 is a close-up perspective view schematic representation of an alternative illustrative embodiment of the outer sheath.

Turning briefly to FIG. 7, there is shown a close-up perspective view schematic representation of an alternative illustrative embodiment of the distal end 54 of the outer sheath 14. In the depicted embodiment, the distal end 54 does not have a narrow portion 58. The distal end 54 of the outer sheath 14 has an insert 62. The insert 62 is preferably composed of non-metal material, such as PEEK. The insert 62 provides an a-traumatic tip to prevent damage at or near the surgical site. For example, the insert 62 is configured to prevent damage to cartilage structures within a joint space. FIG. 7 shows the blade 16 recessed within the insert 62 to allow for introduction of the outer sheath 14 and the blade 16 into the surgical site (e.g., joint space) either with or without a cannula.

Figure 8A:
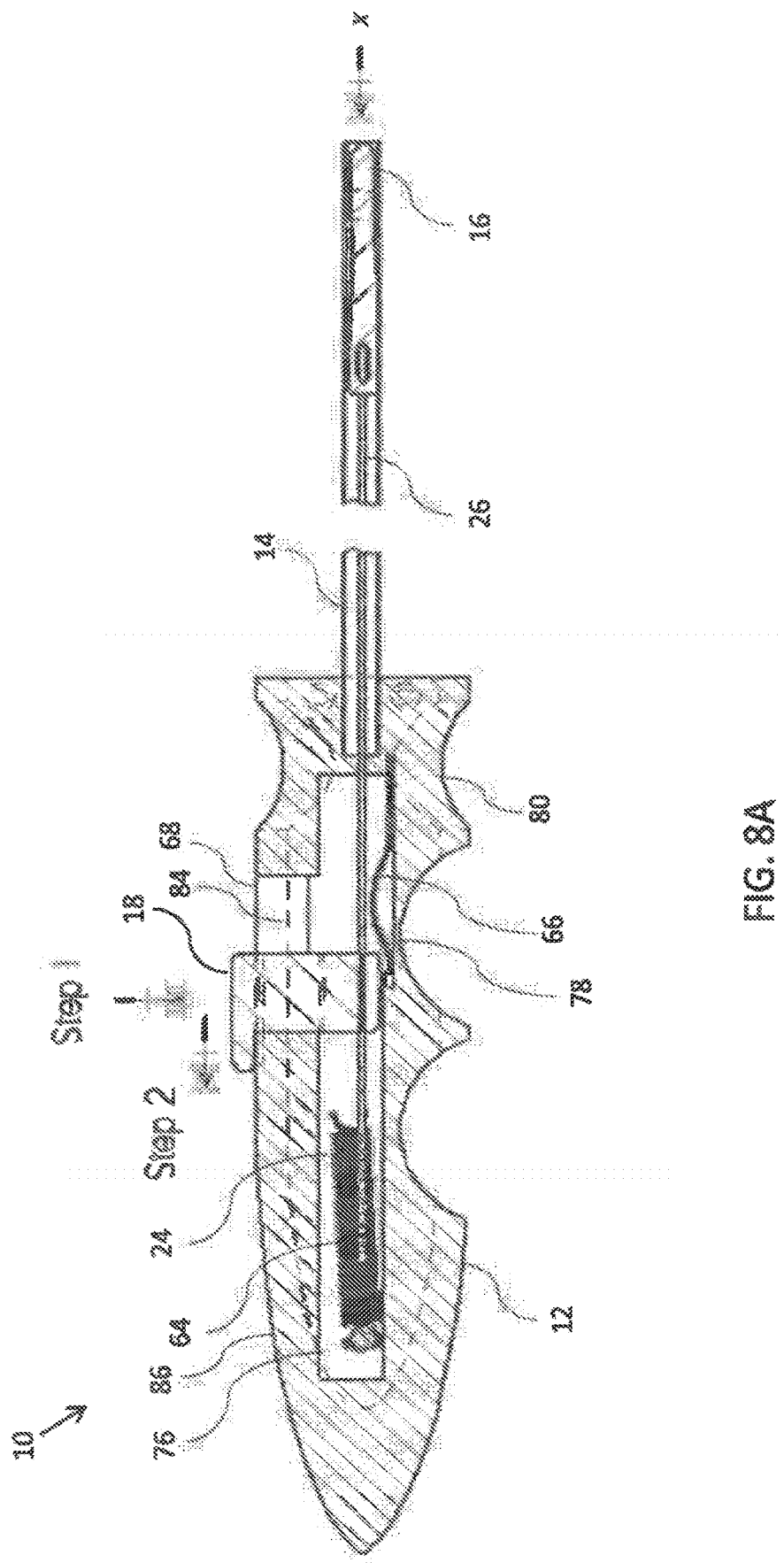
FIG. 8A is a cutaway side view schematic representation of an illustrative embodiment of the retractable surgical cutting device of FIG. 1 in the retracted position.
Figure 8B:
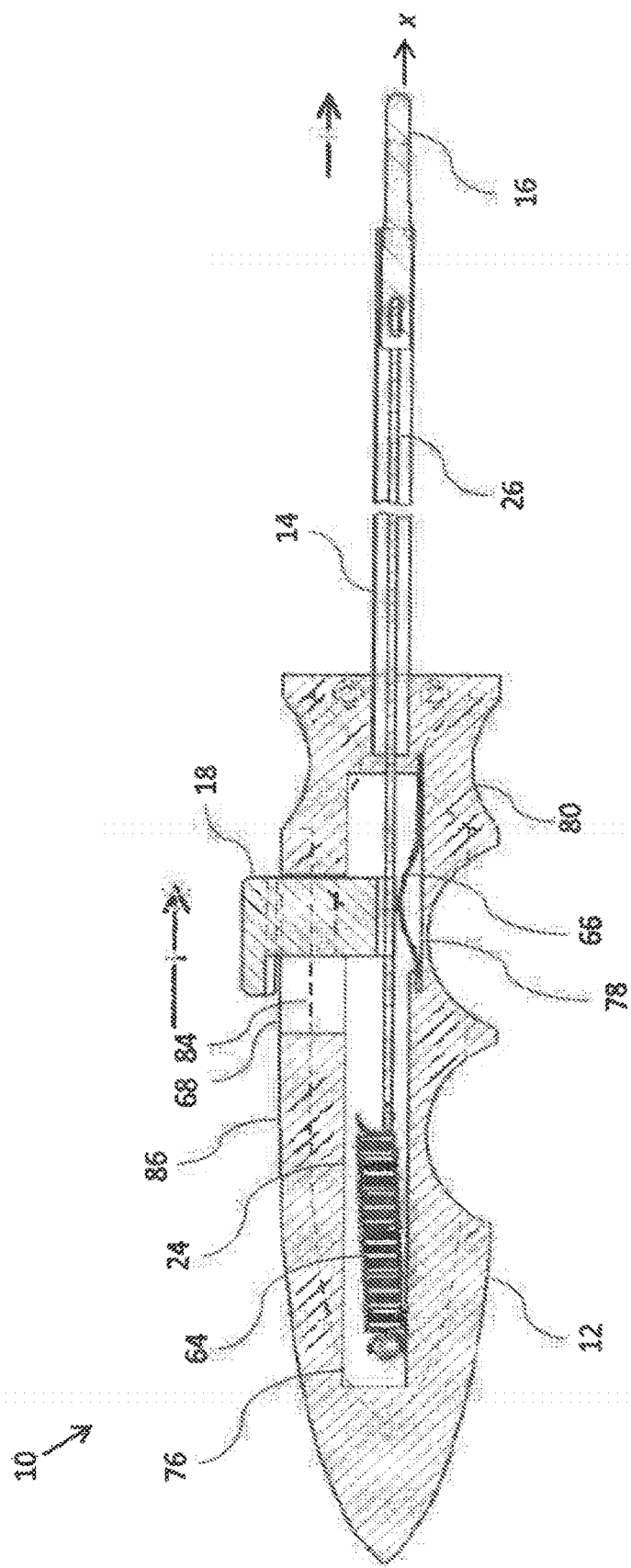
FIG. 8B is a cutaway side view schematic representation of an illustrative embodiment of the retractable surgical cutting device of FIG. 1 in the extended position.

Referring now to FIGS. 8A-8B, there are shown cutaway side view schematic representations of an illustrative embodiment of the retractable surgical cutting device of FIG. 1 in the retracted and extended positions, respectively. The handle 12 comprises a drive mechanism 28 therein, which facilitates movement of the actuator 26 and blade 16 longitudinally in both directions along an x-axis within the outer sheath 14. In the embodiment shown in FIGS. 8A-8B, the drive mechanism 28 comprises a pair of springs. The pair of springs includes an extension spring 64 and a flat spring 66 (or thin metal piece). In the depicted embodiment, the extension spring 64 is a coil spring and the flat spring 66 is a leaf spring. Numerous combinations of springs may be utilized to facilitate movement of the actuator 26 along the first channel 24.

Still referring to FIGS. 8A-8B, the extension spring 64 is connected at a proximal end 76 of the first channel 24 within the handle 12. The extension spring 64 may be attached via a screw or other connector. The free end of the extension spring 64 is connected to the actuator 26. The actuator 26 extends through the first channel 24 over a receptacle 78 in the handle 12, which extends from and is connected to the first channel 24. The flat spring 66 is attached to the receptacle 78 via a screw or other connector. As shown in the depicted embodiment, both the extension spring 64 and the flat spring 66 extend longitudinally along the x-axis.

In one embodiment for assembling the device 10, the proximal end 36 of the actuator 26 is first attached to the switch 18 and hooked onto the extension spring 64. The extension spring 64 is then looped over a post located within the first channel 24 of the handle 12. The flat spring 66 is positioned near a distal end 80 of the handle 12, under the actuator 26. The outer sheath 14 is attached to the handle 12 and the two pieces 20, 22 of the handle 12 are assembled together.

Figure 9:
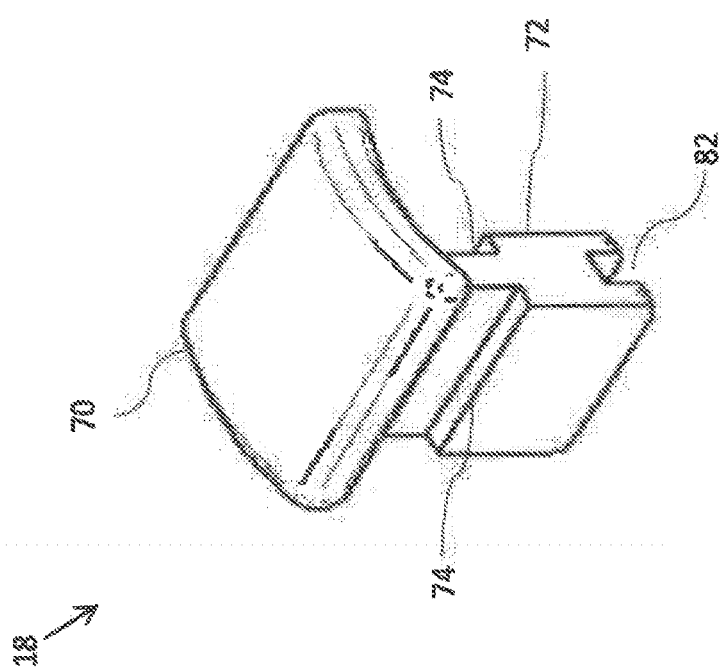
FIG. 9 is perspective view schematic representation of an illustrative embodiment of the switch of the retractable surgical cutting device of FIG. 1.

Still referring to FIGS. 8A-8B, the extension spring 64 is indirectly connected to the switch 18 via the actuator 26 to facilitate longitudinal movement of the actuator 26 along the x-axis. The switch 18 extends from the exterior of the handle 12 through a second channel 68. The second channel 68 extends from the exterior of the handle 12 into the first channel 24. An illustrative embodiment of the switch 18 is shown in FIG. 9. The switch 18 comprises an outer portion 70 connected to a body portion 72. In the depicted embodiment, the outer portion 70 has a width which is greater than the width of the second channel 68 such that the outer portion 70 of the switch 18 is maintained on the exterior of the handle 12 (as shown in FIGS. 8A-8B). Also shown in the embodiment of FIG. 9, the switch 18 has an actuator slot 82 configured for connection to the actuator 26.

Still referring to FIG. 9, the body portion 72 of the switch 18 has a pair of flanges 74. The pair of flanges 74 facilitates movement of the body portion 72 of the switch 18 along the second channel 68. In particular, the flanges 74 and the outer portion 70 of the switch 18 are dimensioned to fit around the interior of the handle 12 on either side of second channel 68 such that the outer portion 70 is above the second channel 68 and the flanges 74 are below the second channel 68 when the device 10 is in the retracted position, as shown in FIG. 8A. In the retracted position, the blade 16 is entirely within the outer sheath 14. The fit of the outer portion 70 and the flanges 74 around the handle 12 on either side of second channel 68 should be loose enough to allow the switch 18 to slide in the longitudinal direction along the x-axis to move the device 10 to the extended position.

In use, when the switch 18 is moved toward the distal end 80 of the handle 12, the extension spring 64 is extended and the switch 18 contacts the flat spring 66, as shown in FIG. 8B. The flat spring 66 forces the switch 18 upward and out through the second channel 68 until at least one of the flanges 74 contacts a shelf 84 within the second channel 68 of the handle 12. In particular, when the switch 18 is forced upward and away from the flat spring 66, at least one of the flanges 74 on the switch 18 interfaces with the shelf 84 in the handle 12 thereby locking the switch 18 in place. The shelf 84 prevents the switch 18 from disconnecting or otherwise falling out from the second channel 68 of the handle 12. When the switch 18 is locked in place against the shelf 84, the device 10 is locked in the extended position. In the extended position, the blade 16 is extended from the outer sheath 14 and exposed for use.

After use, the switch 18 is pressed downward toward the flat spring 66 and moved proximally along the second channel 68. By pressing the switch 18 downward, the flange 74 is released from the shelf 84 and the switch 18 is unlocked or free for movement proximally within the second channel 68. In one embodiment, the device 10 emits an audible indication that the switch 18 has reached the locked and/or unlocked positions. For example, the interfacing between the flange 74 and the shelf 84 may cause an audible clicking sound.

In the embodiment shown in FIGS. 8A-8B, the switch 18 is located on a top side 86 of the device 10. However, the switch 18 can be configured to be positioned at any other location on the device 10, such as the switch 18 in FIG. 10, for example. The embodiment of the switch 18 depicted in FIG. 10 also comprises an outer portion 70 connected to a body portion 72. The body portion 72 of the switch 18 has a pair of flanges 74, which facilitate movement of the body portion 72 of the switch 18 along a second channel 68, similar to the embodiment shown in FIGS. 8A-9.

Figure 10:
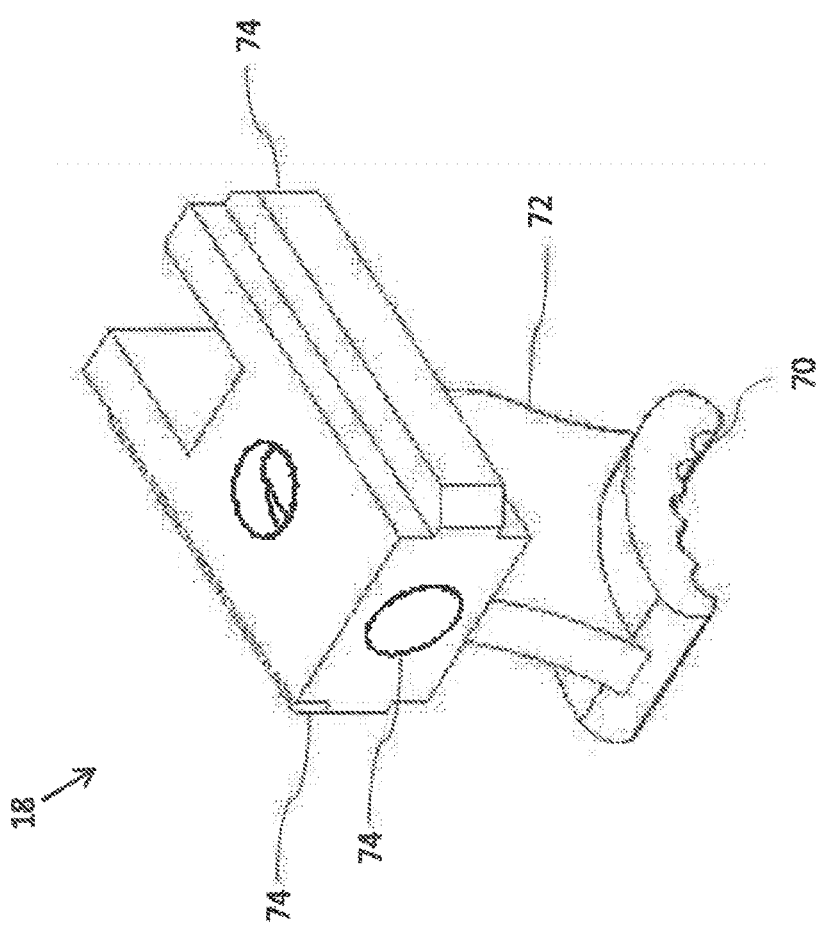
FIG. 10 is perspective view schematic representation of an alternative illustrative embodiment of the switch.
Figure 11:
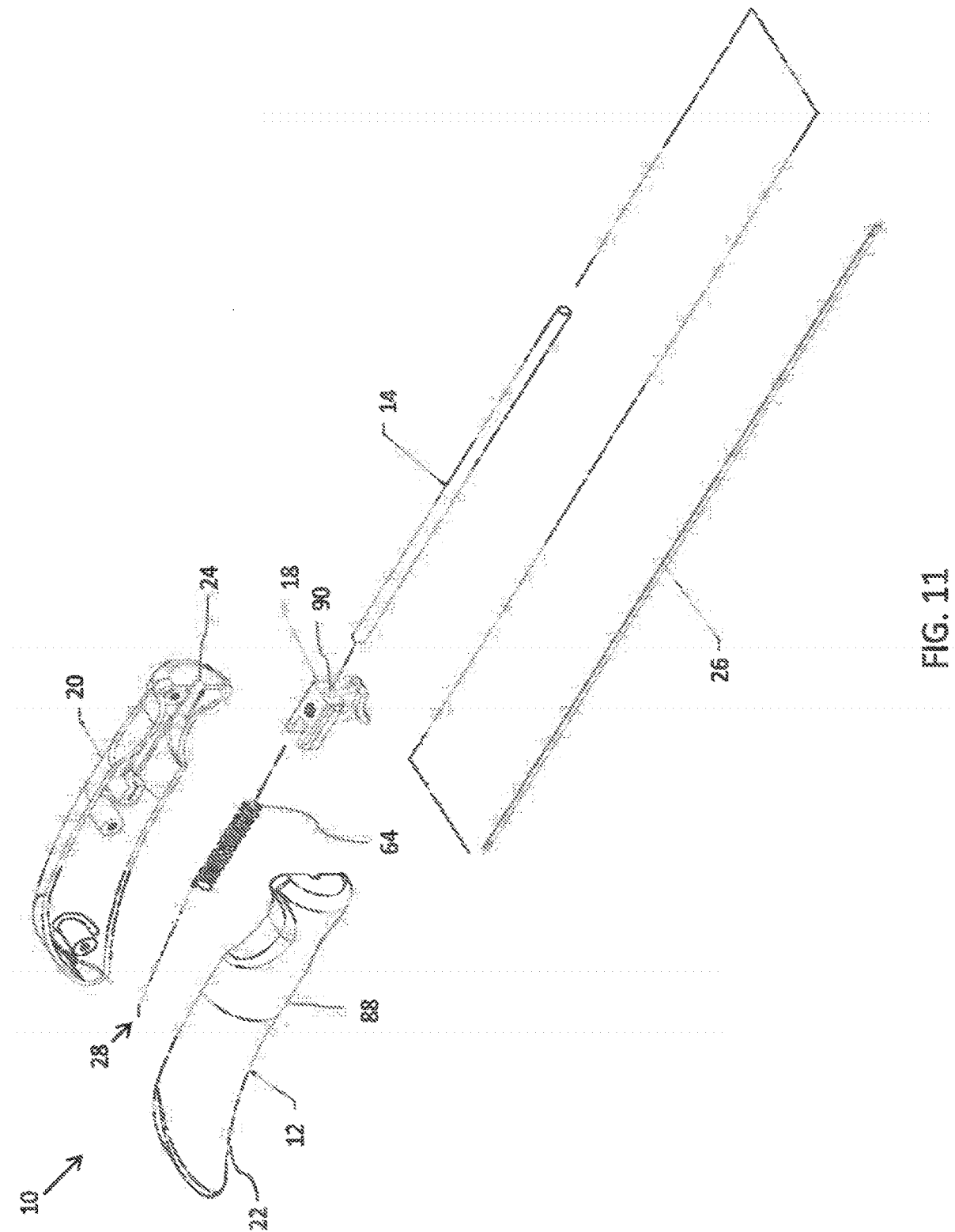
FIG. 11 is an exploded perspective view schematic representation of an alternative illustrative embodiment of the retractable surgical cutting device.

The switch 18 in FIG. 10 can be positioned on a bottom side 88 of the device 10, as shown in FIG. 11. In the embodiment depicted in FIG. 11, the switch 18 is easily accessible to the user as the switch 18 is located near the grip of the user on the handle 12 of the device 10. The first channel 24, which is connected to the actuator 26 in the embodiment shown in FIG. 2, extends through the switch 18 in the embodiment shown in FIG. 11. Specifically, the body portion 72 of the switch 18 in FIG. 10 comprises an aperture 90 for receiving and containing the actuator 26. In the depicted embodiment, the outer sheath 14 is connected to the switch 18, at the outer perimeter of aperture 90, for example.

Figure 12A:
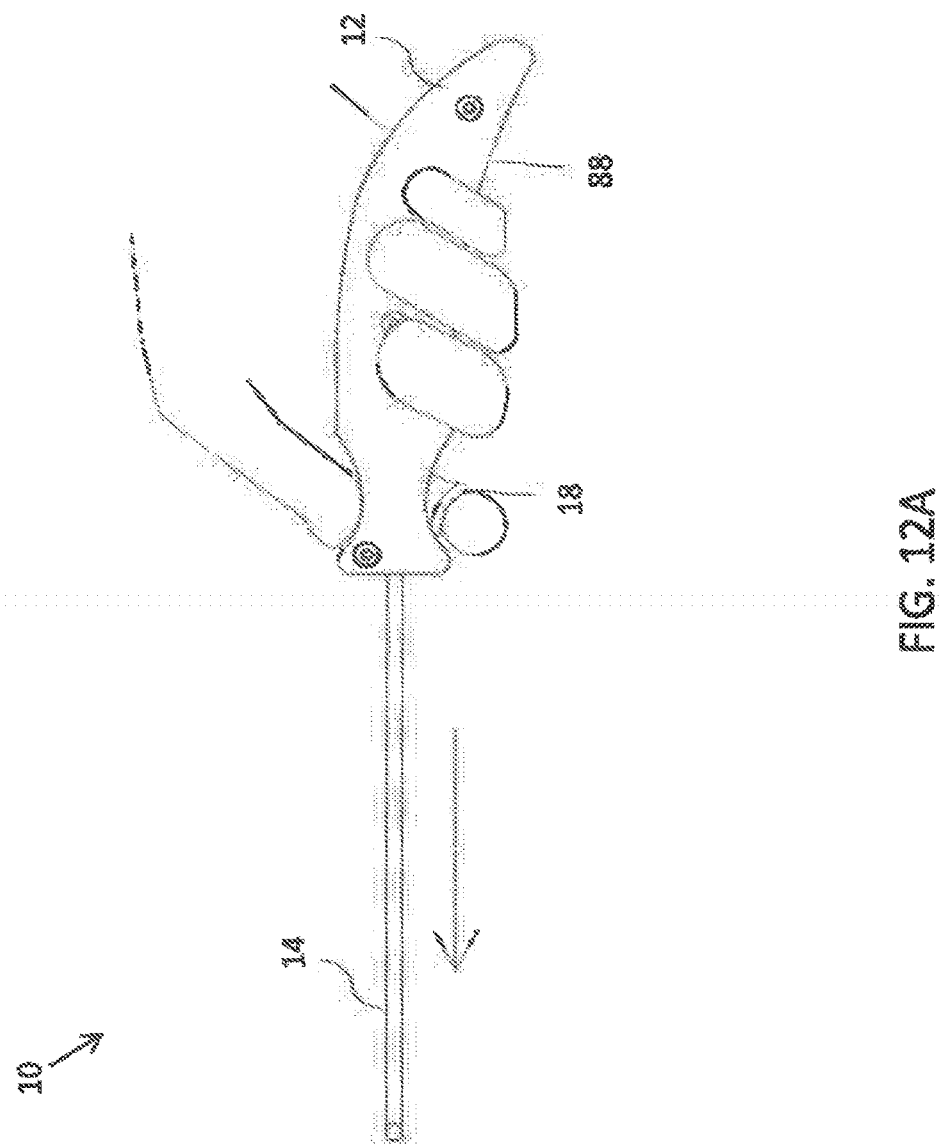
FIG. 12A is a side view schematic representation of an illustrative embodiment of the retractable surgical cutting device of FIG. 11 in the retracted position.
Figure 12B:
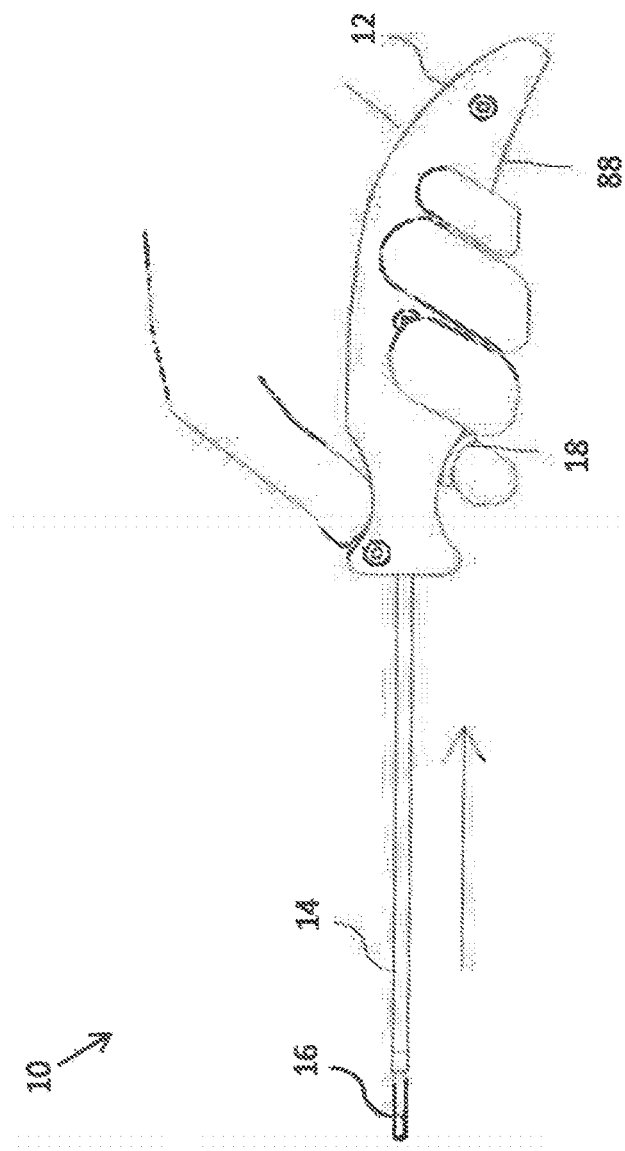
FIG. 12B is a side view schematic representation of an illustrative embodiment of the retractable surgical cutting device of FIG. 11 in the extended position.

Referring now to FIG. 12A, there is shown a side view of an illustrative embodiment of the device in FIG. 11 in the retracted position. In the retracted position, the blade 16 is contained within the outer sheath 14 and the switch 18 is not actuated. From the retracted position, pressing (i.e., actuating) the switch 18 moves the switch 18 proximally within the handle 12. As the switch 18 moves, the switch 18 pulls the connected outer sheath 14 proximally while the actuator 26 remains stationary. Proximal movement of the outer sheath 14 exposes the blade 16 at the distal end 30 of the actuator 26 for use, as shown in FIG. 12B.

Figure 13:
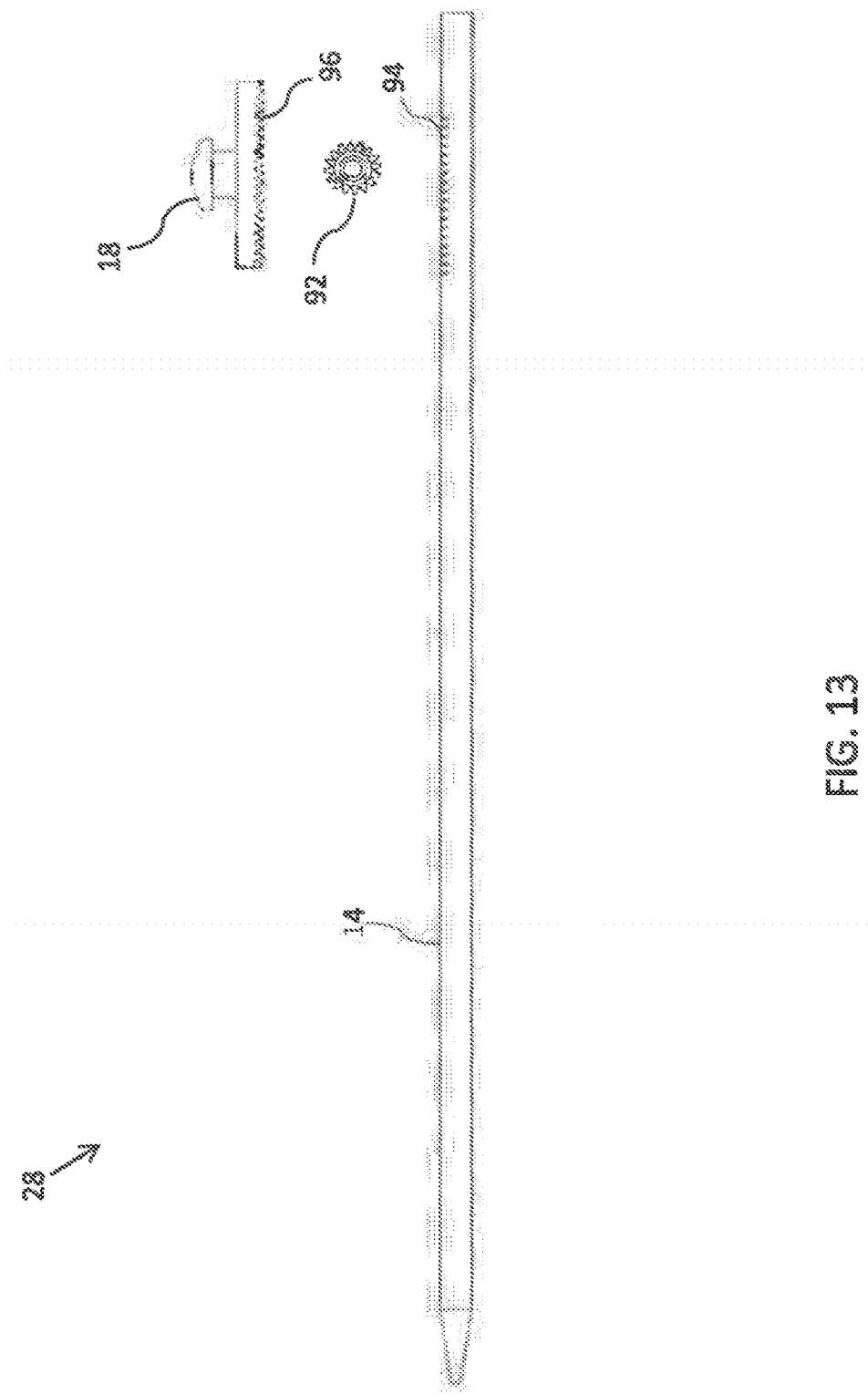
FIG. 13 is an exploded side view schematic representation of an alternative illustrative embodiment of the drive mechanism.
Figure 14:
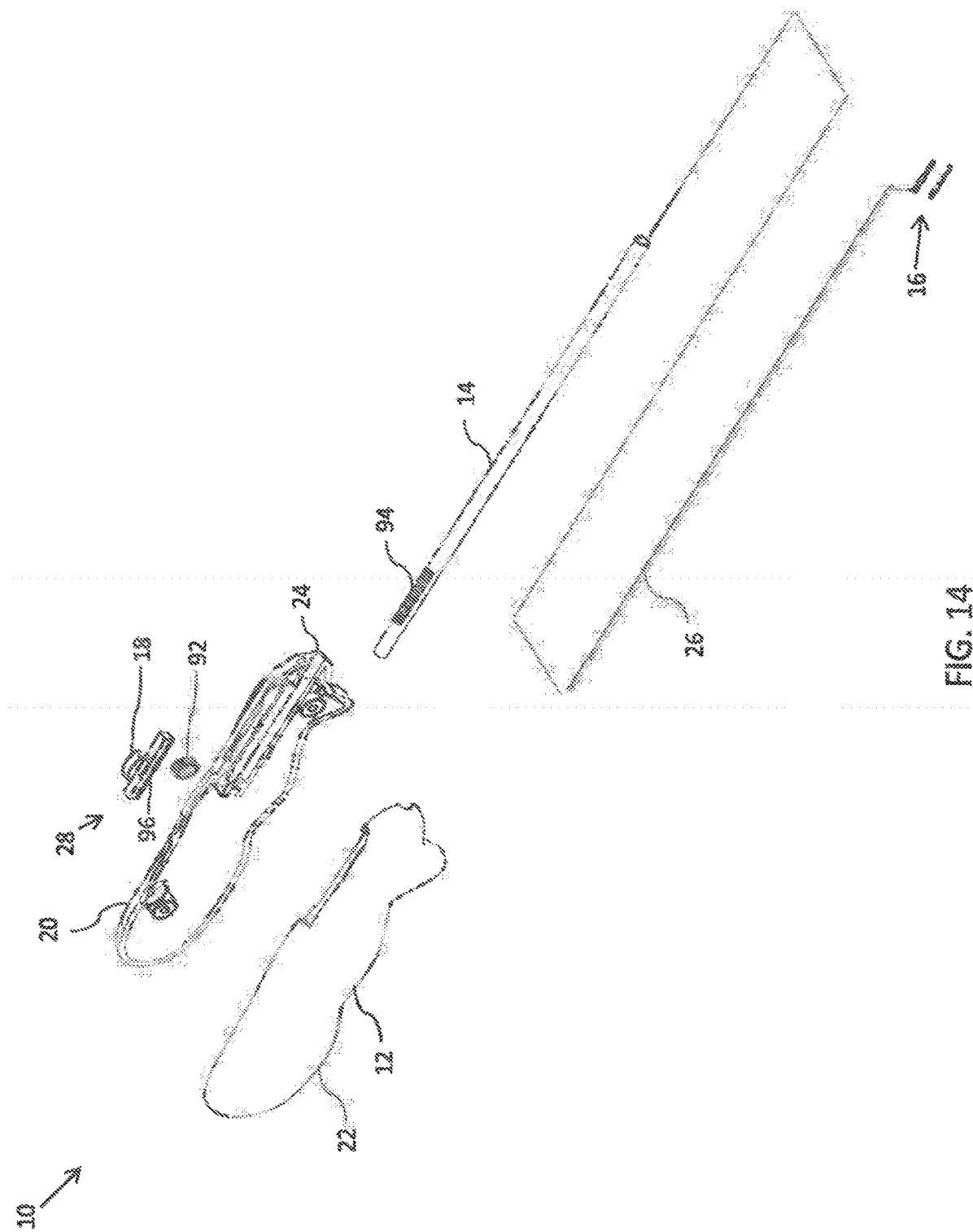
FIG. 14 is an exploded perspective view schematic representation of an illustrative embodiment of the retractable surgical cutting device with the drive mechanism of FIG. 13.
Figure 15:
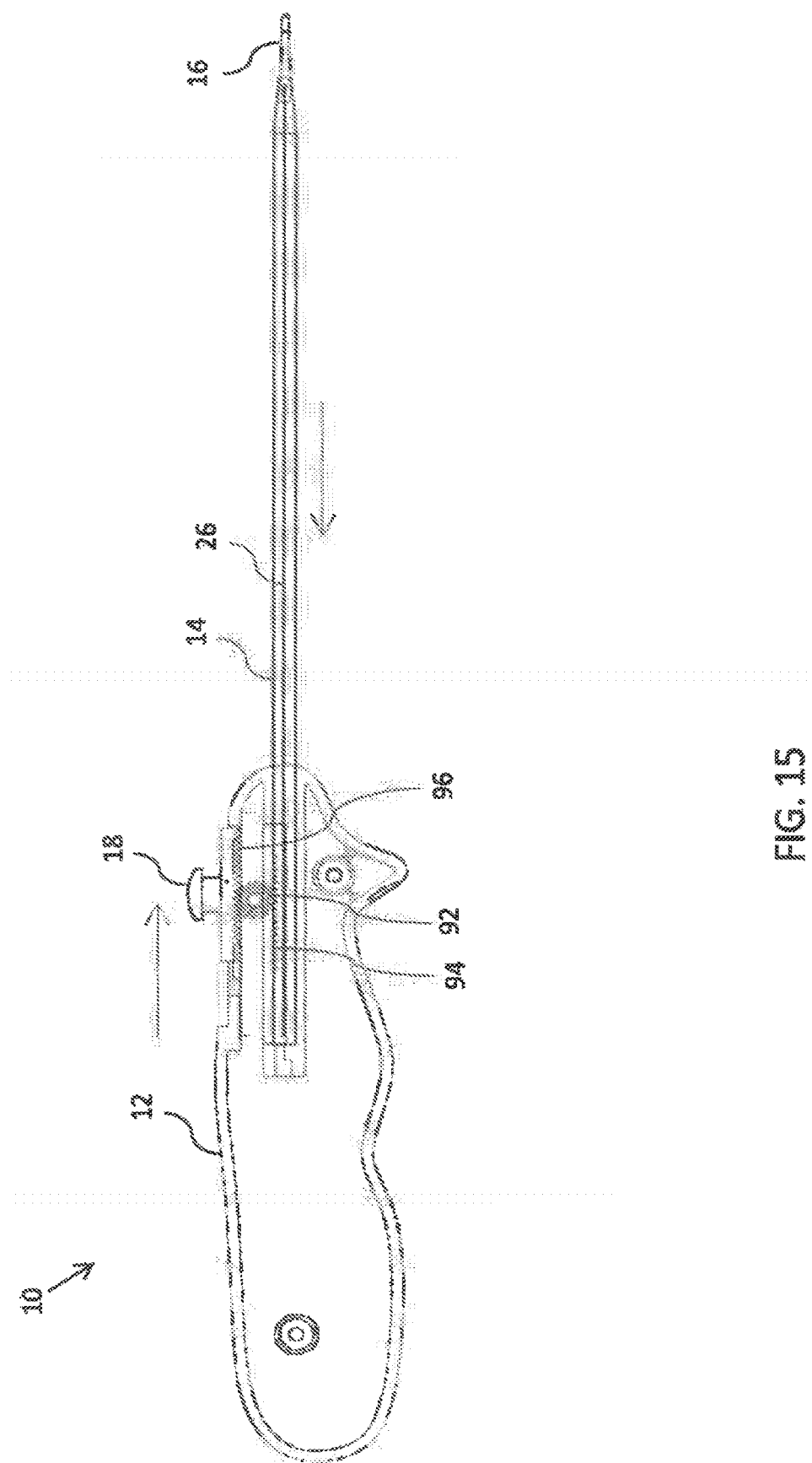
FIG. 15 is a side view schematic representation of an illustrative embodiment of the retractable surgical cutting device of FIG. 14 in the extended position.

Referring now to FIGS. 13-15, there are shown various views of an alternative embodiment for the drive mechanism 28. In the embodiment depicted in FIG. 14, the drive mechanism 28 is a rack and pinion assembly comprising the switch 18, a gear 92, and a rack 94 (or treads) on the outer sheath 14. As shown in FIG. 14, the outer sheath 14 extends through the first channel 24. The rack 94 on the outer sheath 14 interfaces with the gear 92 within the handle 12, which also interfaces with a bottom side 96 of the switch 18. The bottom side 96 of the switch 18 also comprises a rack (or treads), which engages the gear 92. From a retracted position, the switch 18 is moved distally, which causes the bottom side 96 of the switch 18 to rotate the gear 92. Rotation of the gear 92 pulls the outer sheath 14 proximally by the rack 94. As the outer sheath 14 moves proximally into the handle 12, the actuator 26 remains stationary causing exposure of at least a portion of the blade 16, as shown in FIG. 15. According to another embodiment, a locking mechanism is provided which can be actuated by a user to selectively stop the ability of the gear 92 to rotate over the rack 94 (and be reversed/released to allow rotation of the gear 92 over the rack 94). Such a locking mechanism can include a push button, a lever arm, detent or other mechanism, for example, which blocks the gear 92 from rotating over the rack 94 (as should be understood by a person of ordinary skill in the art in conjunction with a review of this disclosure).

Figure 16A:
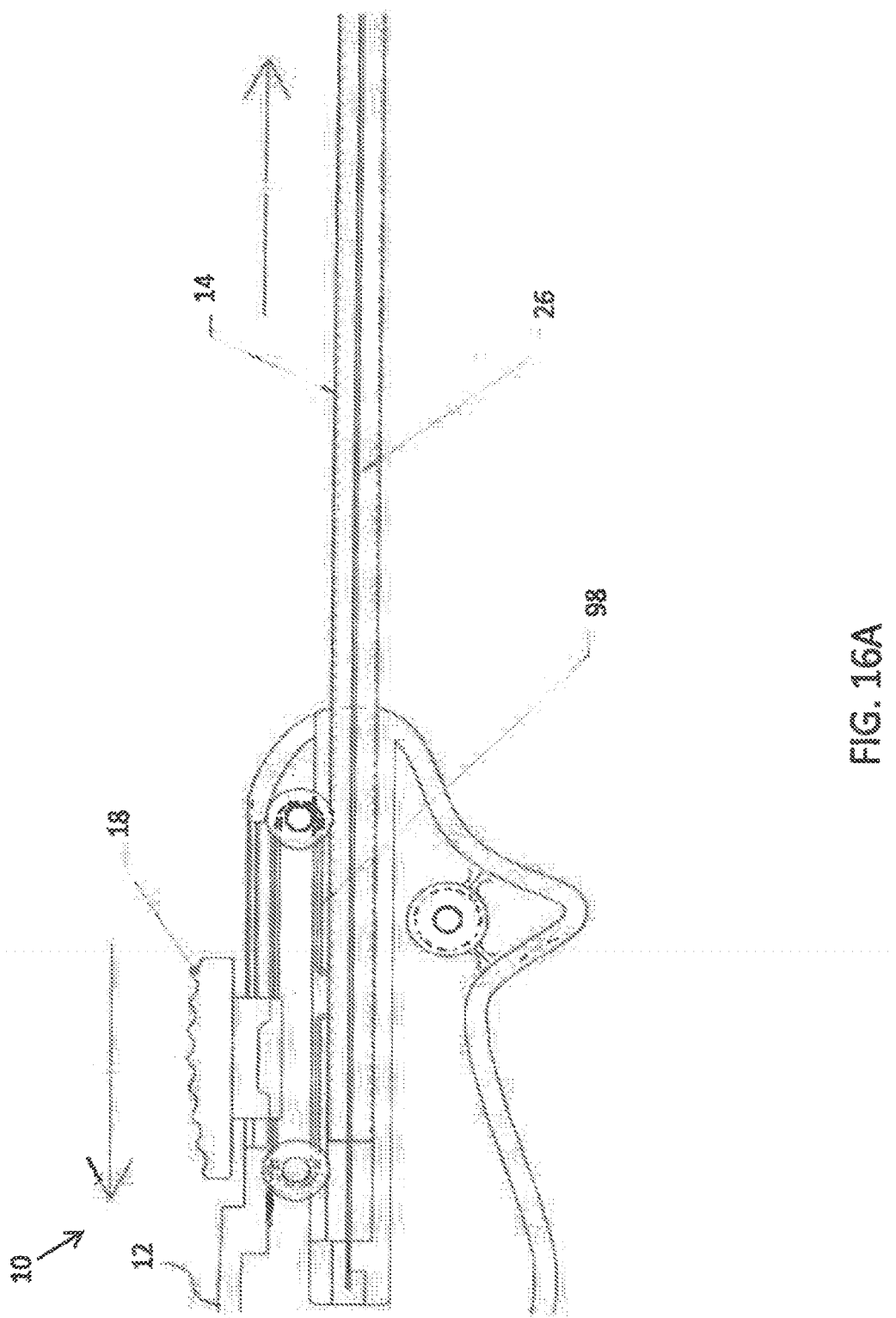
FIG. 16A is a side view schematic representation of an alternative illustrative embodiment of the drive mechanism of the retractable surgical cutting device in the retracted position.
Figure 16B:
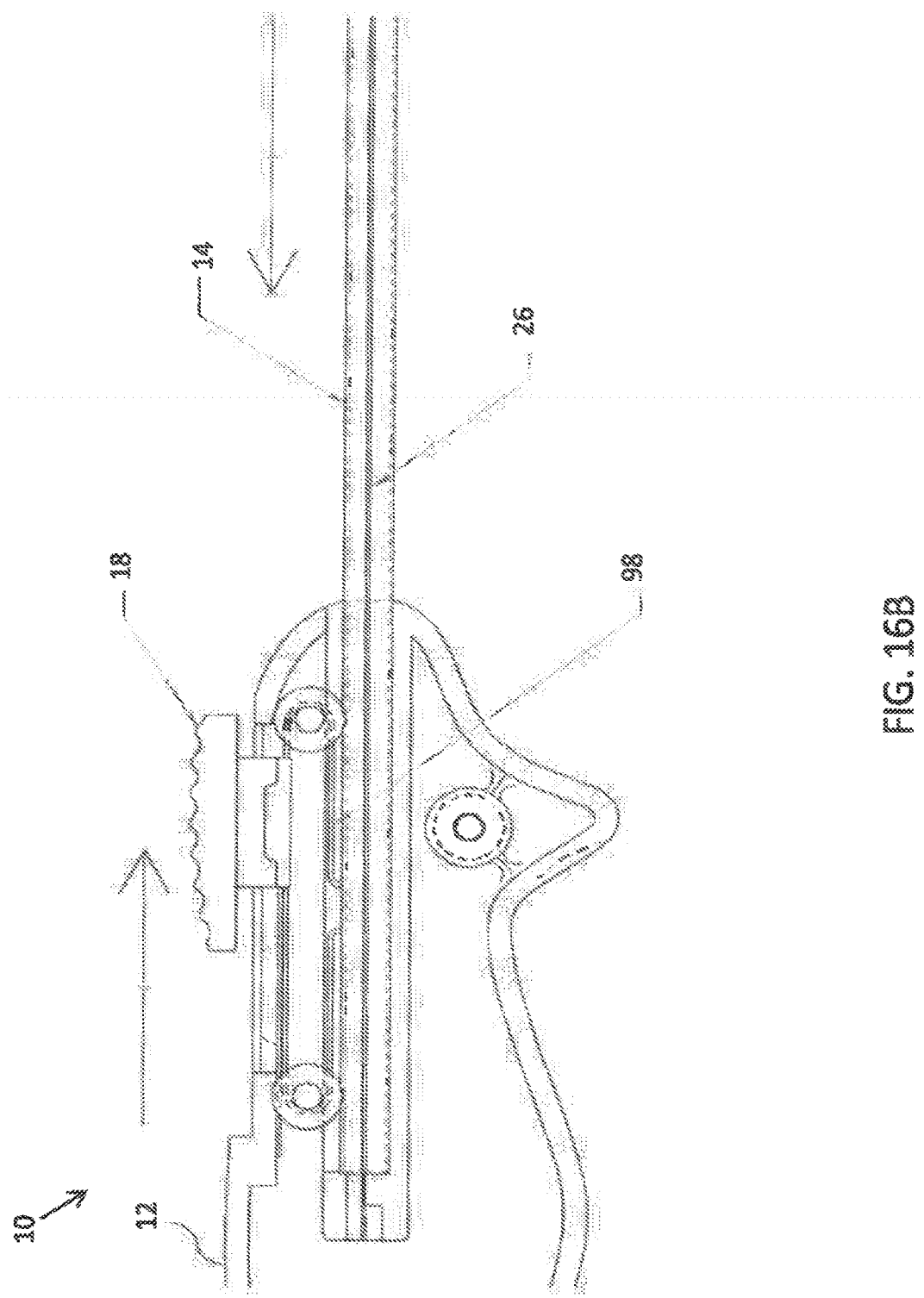
FIG. 16B is a side view schematic representation of an illustrative embodiment of the drive mechanism of the retractable surgical cutting device of FIG. 16A in the extended position

In another embodiment, shown in FIGS. 16A-16B, the drive mechanism 28 is a sliding wire assembly. The sliding wire assembly comprises the switch 18, a wire (or flat stock) 98, and the outer sheath 14. In the depicted embodiment, the wire 98 is attached to both the switch 18 and the outer sheath 14, and is loosely contained by screws, a molded channel, or other known connectors. FIG. 16A shows the device 10 comprising the sliding wire assembly in the retracted position. As the switch 18 is moved distally toward the distal end 30 of the actuator 26 (as shown in FIG. 16B), the wire 98 moves around the screws or within the molded channels, which in turn moves the outer sheath 14 proximally in a direction opposing the direction of movement of the wire 98 and the switch 18. As the outer sheath 14 moves proximally, the actuator 26 remains stationary and the blade 16 is exposed for use. In one embodiment, the wire or flat stock 98 is composed of stainless steel. However, any other suitable compositions may be used.

An embodiment of an actuation and locking mechanism of a retractable surgical cutting device will now be described with reference to additional figures. The manually actuated and retractable surgical device can have some or all of the configurations and attributes of the retractable surgical device described above, some of which will not be repeated below. The main difference is the actuation and locking mechanism, which can be used on conjunction with the previously described embodiments of the retractable surgical device in place of any previously described actuation and/or locking mechanism.

In brief, an embodiment of the actuation and locking mechanism is a Geneva-style actuation/drive and locking mechanism (as should be understood by a person of ordinary skill in the art in conjunction with this disclosure). The Geneva drive and locking mechanism is configured to translate a continuous linear and rotational movement into intermittent rotational and linear movement.

Figure 17:
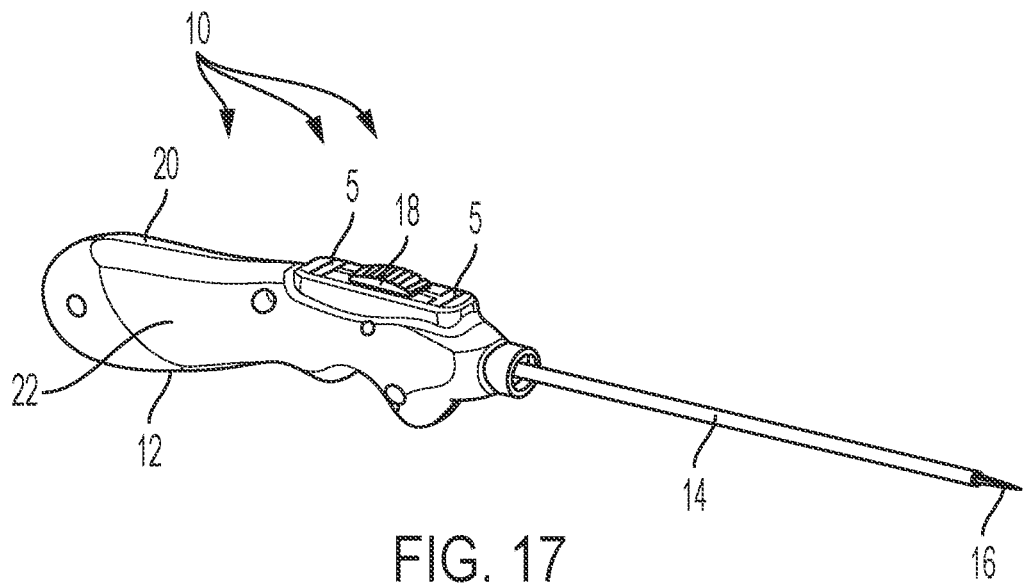
FIG. 17 is a side view schematic representation of an illustrative additional embodiment of a retractable surgical cutting device.

Referring now to FIG. 17, there is shown a side view schematic representation of an illustrative additional embodiment of a retractable surgical cutting device 10. The device 10 extends along a central longitudinal axis and comprises a handle 12 connected to an outer sheath 14, which extends to a distal blade 16. The blade 16 is selectively extended and retracted upon actuation (e.g., sliding in a proximal or distal direction along an axis that is parallel to the central longitudinal axis of the device) of an actuator (here, a button) 18 on the handle 12, as will be explained in detail later. As shown in FIG. 17, the handle 12 can include thumb and finger grooves such that the shape of the handle 12 is ergonomic. The ergonomic design of the handle 12 provides increased control of the device 10 for its intended use. In other embodiments, the handle 12 may have fewer grooves or no grooves entirely. In some embodiments, the handle 12 is composed of plastic; however, the handle 12 may be composed of stainless steel or other traditional materials suitable for surgical devices.

Still referring to FIG. 17, the handle 12 of the device 10 can be comprised of two pieces (or halves of a clamshell), a first piece 20 and a second piece 22, and can have one or more channels therethrough. The button 18 can move distally along an axis parallel to the central longitudinal axis and toward the distal end of the instrument, and can be slid proximally along the axis parallel to the central longitudinal axis and toward the proximal end of the device. At the end of the range of motion of button 18 (distally and proximally on the top surface of the device), there can be small finger-like projections 5, that are configured to provide a minimal amount of friction—only what is necessary to hold the button 18 at the distal and proximal extremities of its travel (it does not restrain the components of the mechanism that are to be actuated). In this embodiment shown, the operation is to alternately actuate the retraction of a protective sheath 14, from shielding a blade 16, at the distal end of the sheath. Alternatively, actuation of the blade 16 beyond the distal end of the sheath 16 and retraction of blade 16 into the sheath 14 (partially and not fully, or fully) is also contemplated.

Figure 18:
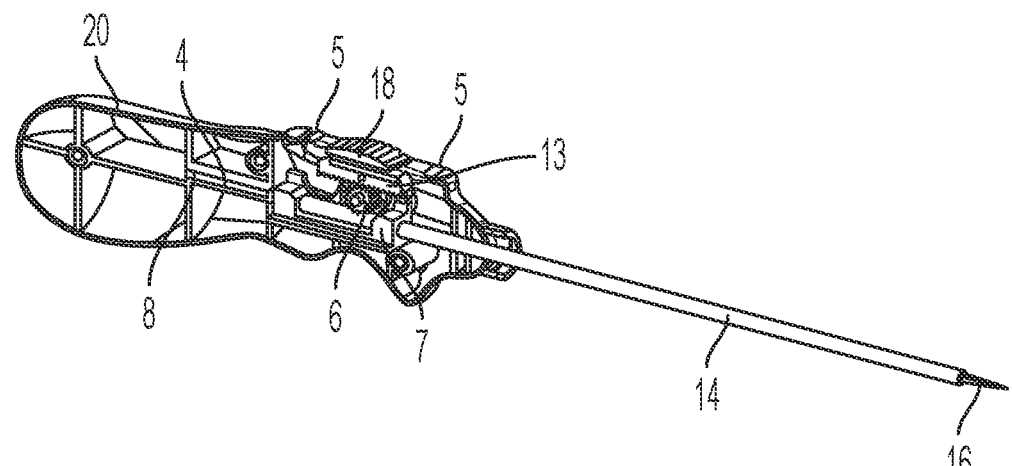
FIG. 18 is a side view open schematic representation of an illustrative embodiment of a retractable surgical cutting device with the second piece of the handle removed.

Turing to FIG. 18, there is shown a side view open schematic representation of an illustrative embodiment of a retractable surgical cutting device 10 with the second piece 22 of the handle 12 removed, according to an embodiment.

FIG. 18 shows the main components of the actuation and locking mechanism of an embodiment. Any number of medical devices could incorporate such an actuation and locking mechanism including, but not limited to, graspers, suture passers, cutting instruments, snipping instruments, etc. Note that the shaft 4 of the cutting blade 16, is rigidly positioned/integrated into the body 20 at its proximal end, by mounting a point 8 of the shaft 4 into the interior of the handle 12, essentially unitizing the two and preventing the shaft 4 (and thus, the blade 16) from moving. In accordance with an embodiment, the actuation and locking mechanism (as described below) is configured to move the sheath 14 proximally and distally along the central longitudinal axis, alternatingly extending it distally and preferably fully over the cutting blade 16 (to protect the user and the patient when not in use), and retracting it proximally to expose the cutting blade 16 for use (essentially, unsheathing it).

The actuation and locking mechanism 100 of an embodiment is partially shown in FIG. 18 and more fully shown in FIGS. 19-22. The actuation and locking mechanism 100 is a Geneva-style actuation/drive and locking mechanism, which is laid out in a linear fashion to create two or more stopping points where component(s) that are moved are locked in position, without any further action of the user beyond the normal user interface, in this case, sliding the button 18. The button 18 is connected (directly molded, or indirectly) to a gear rack 13, which include teeth that mesh with the teeth of a pinion gear 6 positioned inside handle 12. Pinion gear 6 is connected (directly or indirectly) to Geneva wheel 15, which includes a pin 9 and a semicircular cam 17. As shown, the pinion gear 6 is centrally positioned adjacent to a first surface of the Geneva wheel 15, the pin 9 is positioned on the first surface and close/adjacent to the perimeter of the Geneva wheel 15, and the semicircular cam 17 is positioned on the first surface opposite to the pin 9 and a predetermined distance from the perimeter of the wheel 15 (so that the Geneva wheel is optimally workable, as should be understood by a person of ordinary skill in the art in conjunction with a review of this disclosure).

Figure 19:
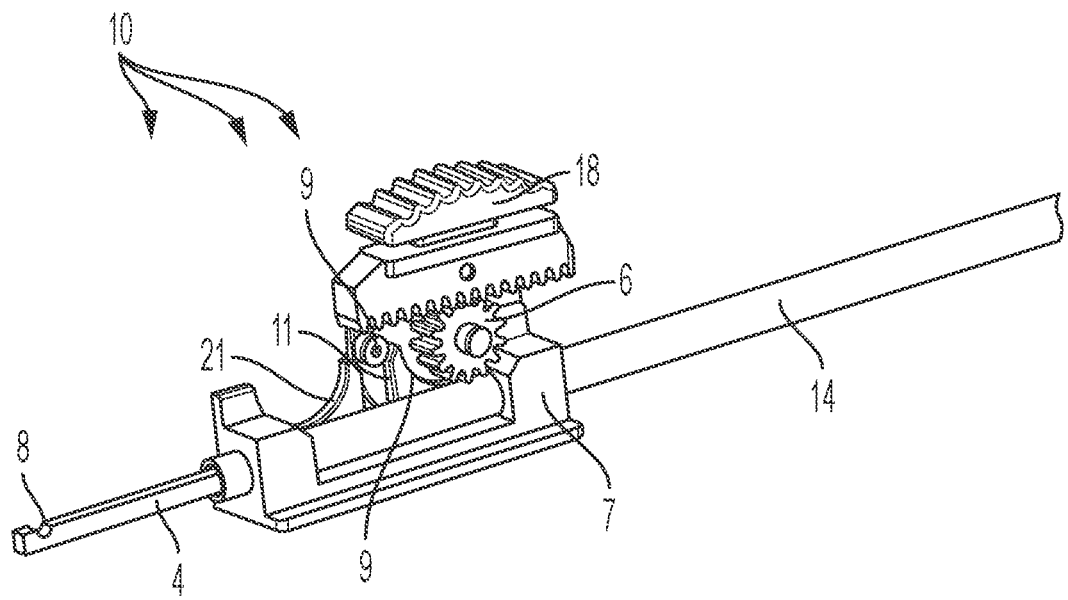
FIG. 19 is a side view schematic representation of an illustrative embodiment of the drive mechanism and slider of the retractable surgical cutting device.

The button 18, gear rack 13, pinion gear 6, wheel 15, pin 9 and semicircular cam 17 act as a drive mechanism for a slider 7. As shown in FIG. 19, for example, slider 7 includes a slot 11 positioned between two semicircular grooves/concave surfaces 9 and 21, respectively (multiple slots and/or more than 2 semicircular grooves/concave surfaces 9 and 21 are contemplated). The slot 11 is configured to receive the pin 9 and the two semicircular grooves/concave surfaces 9 and 21 are configured to receive the semicircular cam 17, upon the movement of the drive mechanism. The slider 7 is moveably attached to the sheath 14, such that when the slider 7 is moved in the proximal or distal direction along the central longitudinal axis by the drive mechanism (the sliding in either direction of button 18 moves the gear rack 13 in the same direction, which causes pinion gear 6 to rotate and spin the wheel 15 to move the semicircular cam 17 into one or more of the semicircular grooves/concave surfaces 9 and 21 and the pin 9 into the slot 11, causing the slider 7 to be moved proximally or distally), the sheath 14 moves in the same direction of the slider 7 to expose or cover the blade 16 (the opposite connections of the sheath 14 and the shaft 4 of the blade 16 (connected to the slider) would result in similar movement of the shaft 14 and blade 16, and fixation of the sheath 14 (connected to the interior surface of the handle)).

Figure 20:
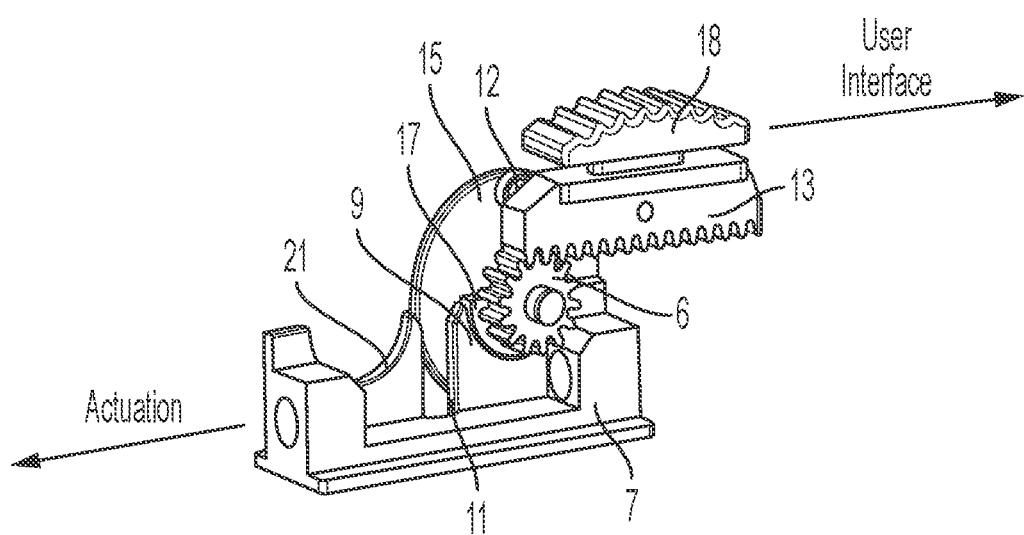
FIG. 20 is a side view schematic representation of an illustrative embodiment of the drive mechanism and slider of the retractable surgical cutting device.
Figure 21:
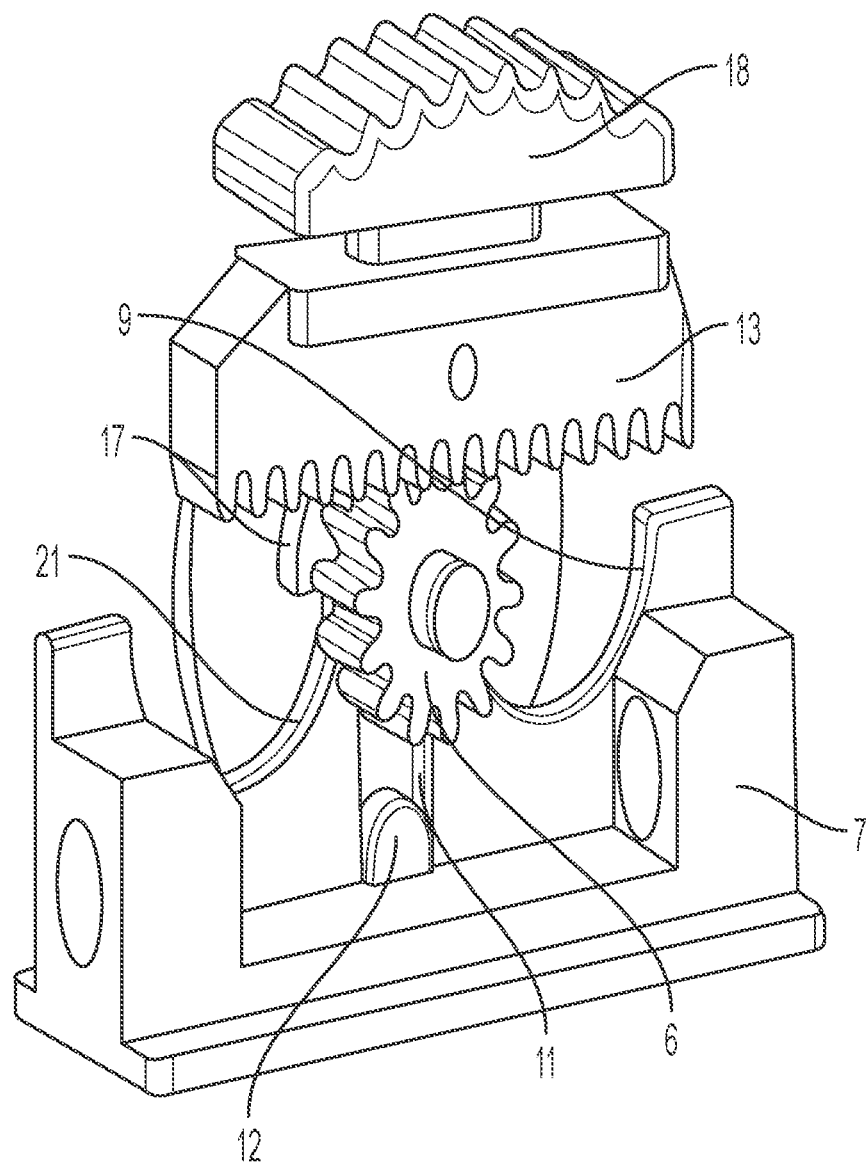
FIG. 21 is a side view schematic representation of an illustrative embodiment of the drive mechanism and slider of the retractable surgical cutting device.
Figure 22:
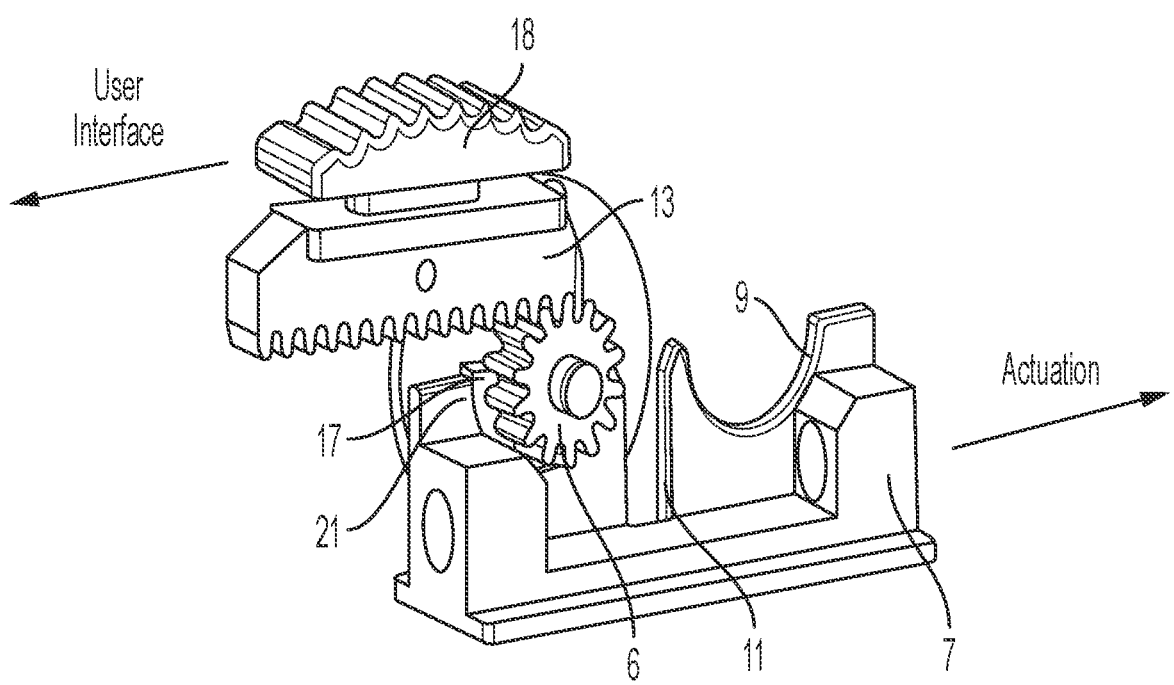
FIG. 22 is a side view schematic representation of an illustrative embodiment of the drive mechanism and slider of the retractable surgical cutting device.

As discussed in more detail with respect to FIGS. 20-22, when pin 12 engages slot 11 of slider 7, pin 12 is configured to drive the slider 7 (and sheath 14) in a proximal or distal direction (depending on movement of the button 18). When the pin is positioned out of the slot 11 and the semicircular cam 17 engages either semicircular grooves/concave surfaces 9 and 21, the slider 7 (and sheath 14) is in a "pause" unmoving/locked configuration and position, while the button 18 continues to move (and the drive mechanism as a whole is still being engaged). The amount of button 18 travel required to pass slider 7, from one position to another can by controlled by characteristics of the teeth on the pinion gear 6, and/or on the gear rack 13. The magnitude of travel of the slider 7 can be altered with the radius of rotation of the pin 12.

Turing to FIG. 20, there is shown a side view schematic representation of an illustrative embodiment of the drive mechanism and slider of the retractable surgical cutting device 10 in accordance with an embodiment. As shown in FIG. 20, a user has interfaced with the button 18, moving it all the way in the direction shown (distally). This movement of button 18 has caused gear rack 13 to move in the same direction with the button 18. Pinion gear 6 has rotated clockwise as shown, per its interface with gear rack 13. The semicircular cam 17 of Geneva wheel 15 is shown nested in the semicircular groove 9, locking the slider 7 into position after its movement in the direction of actuation (proximally), shown with the directional arrow. Notably, the locking of slider 7 occurred with no user action other than sliding the button 18.

Turing to FIG. 21, there is shown a side view schematic representation of an illustrative embodiment of the drive mechanism and slider of the retractable surgical cutting device 10 in accordance with an embodiment. FIG. 21 shows the drive mechanism and slider 7 at the midpoint between two stop/locked positions. Pin 12 on Geneva wheel 15 is positioned in slot 11. As the wheel 15 is rotated by pinion gear 6 interacting with gear rack 13, it passes (pursuant to the drive functionality of the pin's 12 engagement with slot 11) the slider 7 from one position to another (most distal position to most proximal position, and vice versa). Note that semicircular cam 17 on the wheel 15 has rotated out of the way of the slot 11 and semicircular grooves 9 of slider 7, as to not impede the movement of slider 7 in the proximal direction (from the position shown in FIG. 20).

Referring to FIG. 22, there is shown a side view schematic representation of an illustrative embodiment of the drive mechanism and slider of the retractable surgical cutting device 10 in accordance with an embodiment. As shown in FIG. 21, the drive mechanism has been fully actuated in the opposite direction shown in FIG. 20. The semicircular cam 17 of wheel 15 is now nested in semicircular groove 21, not in semicircular groove 9 as shown earlier in FIG. 20. The slider 7 is now actuated and locked into the "distal" position by no user action other than sliding the button 18 in the proximal direction.

While any number of materials could be used to fabricate such an actuation and locking mechanism, it is anticipated that typically the mechanism as a whole, and it's housing can be fabricated of injection molded plastic of reasonable strength, and that the aspects of the medical instrument to be actuated, such as cutters, blades, snippers, suture passers, etc., can be made of surgical grade metals such as stainless steel and Nitinol.

The inventors contemplate various alternative embodiments of the actuation and locking mechanism described herein. For example, as previously noted, a slider 7 with a plurality of slots 11 and/or more than two semicircular grooves 9 and 21, in order to create more than two paused/locked stopping locations for a mechanism's actuation where intermediate stages of movement that are locked in place are desired.

The embodiment of the actuation and locking mechanism described herein creates a "reversing" effect, where direction of the button 18, in one direction generates motion of the slider 7 in the opposite direction. This is because the gear rack 13 and the slider 7 are on opposite sides of the pinion gear 6. An alternative embodiment can have the gear rack 13, and slider 7 on the same side of the pinion gear 6, eliminating the reversing effect and causing the slider 7 to move in the same direction as the button 18.

While the of the actuation and locking mechanism described herein has a linear relationship between button 18 motion and pinion gear 6 rotation, an alternate embodiment is possible where pinion gear 6 is non-circular and gear rack 13 is a non-linear shape suitable for interfacing with a non-circular pinion gear. This would result in an alteration of the motion profile of the slider 7 with respect to movement of the button 18.

The described embodiment of the actuation and locking mechanism shows one rack 13, one pinion gear 6, and one Geneva wheel 15, acting on one slider 7. An alternate embodiment is possible where more than one gear rack is moved by a single button 18, and those gear racks interact with more than more than one pinion gear, more than one Geneva wheel, and more than one slider, to actuate more than one mechanism, and that the relative timing of these systems can cause multiple motions that can be orchestrated in a particular sequence to perform more complicated systems of actuations. For example, if one desired a sheathed snipper where the cutting elements of the snipper could only possibly actuate and de-actuate after the sheath was moved to a fully retracted position and never when the sheath was extended, a single button 18 could move two gear racks that interact with two pinion gears, two Geneva wheels, and two sliders, where the two systems could be timed with respect to each other as to be out of phase with each other in order to orchestrate the desired sequence of motions needed to ensure that snipper actuation and de-actuation could only occur after sheath retraction had occurred (as should be understood by a person of ordinary skill in the art in conjunction with a review of this disclosure). This timing between the two systems actuated by the same button could be achieved by altering any number of design parameters, such as the angular timing of each pinion's teeth with respect to its respective rack, alternating the pitch diameter and/or number of teeth on each pinion gear, alternating the magnitude (radius about which the pin rotates) of the motion developed by pin 12, alternating the number of slots and semicircular grooves in the sliders (as should be understood by a person of ordinary skill in the art in conjunction with a review of this disclosure). While any number of variations could be utilized to achieve multiple varying motion profiles and orchestrate those multiple motion profiles with respect to each other, the essence of this embodiment is that multiple Geneva-based mechanisms actuated by a single button can generate multiple motion profiles to create more complex systems of coordinated motions between multiple functionalities incorporated in a product (as should be understood by a person of ordinary skill in the art in conjunction with a review of this disclosure).

In an alternate embodiment, the linear motion of the gear rack 13 acted upon by a button 18 is replaced with an arc-shaped gear rack actuated by a lever, which causes the teeth of the arc-shaped gear rack to rotate the pinion gear 6.

All definitions, as defined and used herein, should be understood to control over dictionary definitions, definitions in documents incorporated by reference, and/or ordinary meanings of the defined terms.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A retractable surgical cutting device, comprising:
   a handle including a handle proximal end, a handle distal end, an outer surface, and an internal space, the handle extending along a central longitudinal axis;
   an actuator located and movable in a first direction to a first actuator position and in a second direction to a second actuator position on the outer surface of the handle;
   a sheath extending along the central longitudinal axis and including a sheath proximal end and a sheath distal end, wherein the sheath proximal end is positioned within the internal space of the handle, and wherein the sheath is configured to move in the first direction to a sheath first position, and is configured to move in a second direction to a sheath second position;
   a shaft at least partially positioned within the sheath and extending along the central longitudinal axis and including a shaft proximal end and a shaft distal end, wherein the shaft proximal end is connected to an interior surface of the handle and the shaft distal end includes a blade; and
   a drive and locking mechanism connected to the actuator and to the sheath within the internal space of the handle, wherein the drive and locking mechanism is configured to move the sheath in the first direction and lock the sheath in the sheath first position in response to movement of the actuator in one of the first direction or the second direction, and wherein the drive and locking mechanism is configured to move the sheath in the second direction and lock the sheath in the sheath second position in response to movement of the actuator in the other one of the first direction or the second direction;
   wherein the drive and locking mechanism is configured to translate a continuous linear movement of the actuator into intermittent linear movement of the sheath;
   wherein the drive and locking mechanism further comprises a gear rack connected to the actuator and having teeth positioned on a surface opposite a surface connected to the actuator, wherein the gear rack is positioned within the internal space of the handle and the gear rack is configured to move with the actuator.

2. The device of claim 1, wherein when the sheath moves in the first direction to the sheath first position, the blade is configured to be positioned within the distal end of the sheath.

3. The device of claim 1, wherein when the sheath moves in the second direction to the second position, the blade is configured to be positioned beyond the distal end of the sheath.

4. The device of claim 1, wherein the drive and locking mechanism further comprises a pinion gear having teeth, wherein:
   the pinion gear is positioned within the internal space of the handle;
   the teeth of the pinion gear mesh with the teeth of the gear rack; and
   the pinion gear is configured to spin upon movement of the gear rack.

5. The device of claim 4, wherein the drive and locking mechanism further comprises a Geneva wheel comprising a perimeter and a first surface and being connected to the pinion gear, wherein:

a pin is positioned on the first surface adjacent to the perimeter;

a semicircular cam is positioned on the first surface opposite to the pin and a predetermined distance from the perimeter of the Geneva wheel; and the Geneva wheel is configured to spin upon the spinning movement of the pinion gear.

6. The device of claim 5, wherein the drive and locking mechanism further comprises a slider attached to the proximal end of the sheath within the internal space of the handle, wherein:

the slider includes at least two semicircular grooves, and at least one slot positioned between the at least two semicircular grooves;

when the pin moveably engages the at least one slot, the slider and sheath are configured to move in the first direction or in the second direction; and when the semicircular cam moveably engages one of the at least two semicircular grooves, the slider and sheath are configured to not move in the first direction or in the second direction.

7. A retractable surgical cutting device, comprising:

a handle including a handle proximal end, a handle distal end, an outer surface, and an internal space, the handle extending along a central longitudinal axis;

an actuator located and movable in a first direction to a first actuator position and in a second direction to a second actuator position on the outer surface of the handle;

a sheath extending along the central longitudinal axis and including a sheath proximal end and a sheath distal end, wherein the sheath proximal end is positioned within the internal space of the handle, and wherein the proximal end of the sheath is connected to the interior surface of the handle;

a shaft at least partially positioned within the sheath and extending along the central longitudinal axis and including a shaft proximal end and a shaft distal end, wherein the shaft is configured to move in the first direction to a shaft first position, and is configured to move in a second direction to a shaft second position; and a drive and locking mechanism connected to the actuator and to the shaft within the internal space of the handle, wherein the drive and locking mechanism is configured to move the shaft in the first direction and lock the shaft in the shaft first position in response to movement of the actuator in one of the first direction or the second direction, and wherein the drive and locking mechanism is configured to move the shaft in the second direction and lock the shaft in the shaft second position in response to movement of the actuator in the other one of the first direction or the second direction;

wherein the drive and locking mechanism is configured to translate a continuous linear movement of the actuator into intermittent linear movement of the shaft;

wherein the drive and locking mechanism further comprises a gear rack connected to the actuator and having teeth positioned on a surface opposite a surface connected to the actuator, wherein the gear rack is positioned within the internal space of the handle and the gear rack is configured to move with the actuator.

8. The device of claim 7, wherein when the shaft moves in the first direction to the first shaft position, wherein the shaft distal end includes a blade and the blade is configured to be positioned within the distal end of the sheath.

9. The device of claim 7, wherein when the shaft moves in the second direction to the shaft second position, wherein the shaft distal end includes a blade and the blade is configured to be positioned beyond the distal end of the sheath.

10. The device of claim 7, wherein the drive and locking mechanism further comprises a pinion gear having teeth, wherein:

the pinion gear is positioned within the internal space of the handle;

the teeth of the pinion gear mesh with the teeth of the gear rack; and the pinion gear is configured to spin upon movement of the gear rack.

11. The device of claim 10, wherein the drive and locking mechanism further comprises a Geneva wheel comprising a perimeter and a first surface and being connected to the pinion gear, wherein:

a pin is positioned on the first surface adjacent to the perimeter;

a semicircular cam is positioned on the first surface opposite to the pin and a predetermined distance from the perimeter of the Geneva wheel; and the Geneva wheel is configured to spin upon the spinning movement of the pinion gear.

12. The device of claim 11, wherein the drive and locking mechanism further comprises a slider attached to the proximal end of the shaft within the internal space of the handle, wherein:

the slider includes at least two semicircular grooves, and at least one slot positioned between the at least two semicircular grooves;

when the pin moveably engages the at least one slot, the slider and shaft are configured to move in the first direction or in the second direction; and when the semicircular cam moveably engages one of the at least two semicircular grooves, the slider and shaft are configured to not move in the first direction or in the second direction.

* * * * *